United States Patent [19]
Vahlne et al.

[11] Patent Number: 5,840,313
[45] Date of Patent: Nov. 24, 1998

[54] PEPTIDES FOR USE IN VACCINATION AND INDUCTION OF NEUTRALIZING ANTIBODIES AGAINST HUMAN IMMUNODEFICIENCY VIRUS

[75] Inventors: Anders Vahlne, Hovås; Bo Syennerholm, Göteborg; Lars Rymo, Hovås; Stig Jeansson; Peter Horal, both of Göteborg, all of Sweden

[73] Assignee: Syntello Vaccine Development KB, Gothenburg, Sweden

[21] Appl. No.: 493,235

[22] Filed: Jun. 20, 1995

Related U.S. Application Data

[63] Continuation of Ser. No. 48,976, Apr. 16, 1993, abandoned, which is a continuation-in-part of Ser. No. 8,092, Jan. 22, 1993, abandoned, which is a continuation of Ser. No. 589,422, Sep. 27, 1990, abandoned.

[51] Int. Cl.$^6$ .......................... A61K 39/21; A61K 38/00; A61K 39/00; C07K 5/00
[52] U.S. Cl. .................................. 424/208.1; 424/188.1; 424/184.1; 424/204.1; 530/324
[58] Field of Search ............................. 424/188.1, 208.1; 530/324

[56] References Cited

FOREIGN PATENT DOCUMENTS

| | | |
|---|---|---|
| 0 330 359 A2 | 8/1989 | European Pat. Off. . |
| WO 86/02383 | 4/1986 | WIPO . |
| WO 87/07616 | 12/1987 | WIPO . |
| WO 89/10416 | 11/1989 | WIPO . |

OTHER PUBLICATIONS

"HIV Binding to the CD4 Molecule: Conformation Dependence and Binding Inhibition Studies" McDougal, et al., *Human Retrovirues, Cancer and AIDS: Approaches to Prevention & Therapy*, pp. 269–281 (1988).

"Polyvalent Human Immunodeficiency Virus Synthetic Immunogen Comprised of Envelope gp120 T Helper Cell Sites and B Cell Neutralization Epitopes".

Palker, et al., *Journal of Immunology*, 142:3612–3619, No. 10 (May 15, 1989).

"Jitters Jeopardize AIDS Vaccine Trials" Cohen, *Science*, 262:980–981 (Nov. 12, 1993).

"Comparative Analysis of HIV–Specific CTL Activity in Lymphoid Tissue and Peripheral Blood" Butini, et al., *Journal of Cellular Biochemistry*, Supplement 18B, J306, p. 147 (Jan. 21–Feb. 13, 1994).

Ho, et al, 1988, "Second Conserved Domain . . . " Science 239:1021–1023.

Haynes, 1993, "Scientific and Social Issues . . . " Science 260: 1279–1286.

Fox, 1994, "No Winners Against AIDS" Biotechnology 12:128.

*Primary Examiner*—Lynette F. Smith
*Attorney, Agent, or Firm*—Knobbe, Martens, Olson & Bear

[57] ABSTRACT

Novel peptides are disclosed which correspond to epitopes of the HIV-1 gp120 protein. These antigenic peptides induce antibody-dependent cellular cytotoxicity against HIV, and thus are useful in immunization against HIV infection and induction of a heightened immune response to HIV.

11 Claims, No Drawings

PEPTIDES FOR USE IN VACCINATION AND INDUCTION OF NEUTRALIZING ANTIBODIES AGAINST HUMAN IMMUNODEFICIENCY VIRUS

RELATED APPLICATIONS

This application is a continuation of U.S. patent application Ser. No. 08/048,976, filed Apr. 16, 1993 now abandoned, which is a continuation-in-part of U.S. patent application Ser. No. 08/008,092, filed Jan. 22, 1993 now abandoned, which is a continuation of U.S. patent application Ser. No. 07/589,422, filed Sep. 27, 1990, now abandoned.

BACKGROUND OF THE INVENTION

The present invention relates to peptides suitable for use in vaccination against AIDS.

The human immunodeficiency virus (HIV) is responsible for the disease that has come to be known as acquired immune deficiency syndrome (AIDS). Although initially recognized in 1981, no cure has yet been found for this inevitably fatal disease. HIV is spread by a variety of means such as sexual contact, infected blood or blood products and perinatally. Due to the complexity of HIV infection and the paucity of effective therapies, eradication of AIDS will most likely occur by preventing new infections rather than curing those persons already infected. To this end a great deal of effort has been expended in developing methods for detecting and preventing infection. Diagnostic procedures have been developed for identifying infected persons, blood and other biological products.

Like most viruses, HIV often elicits the production of neutralizing antibodies. Unlike many other viruses and other infectious agents for which infection leads to protective immunity, however, HIV specific antibodies are insufficient to halt the progression of the disease. Therefore, in the case of HIV, a vaccine that elicits the immunity of natural infection could prove to be ineffective. In fact, vaccines prepared from the HIV protein gp160 appear to provide little immunity to HIV infection although they elicit neutralizing antibodies. The failure to produce an effective anti-HIV vaccine has led to the prediction that an effective vaccine will not be available until the end of the 1990's.

The HIV genome has been well characterized. Its approximately 10 Kb encodes sequences that contain regulatory segments for HIV replication as well as the gag, pol and env genes coding for the core proteins, the reverse transcriptase-protease-endonuclease, and the internal and external envelope glycoproteins respectively.

The HIV env gene encodes the intracellular glycoprotein, gp160, which is normally processed by proteolytic cleavage to form gp120, the external viral glycoprotein, and gp41, the viral transmembrane glycoprotein. The gp120 remains associated with HIV virions by virtue of noncovalent interactions with gp41. These noncovalent interactions are weak, consequently most of the gp120 is released from cells and virions in a soluble form.

Previous studies have shown that the proteins encoded by the gag and especially the env regions of the HIV-1 genome are immunogenic since antibodies to the products of the gag and env genes are found in the sera of HIV infected, AIDS and ARC ("AIDS Related Condition") patients.

It has previously been shown that some antibodies obtained from sera of AIDS and ARC patients, as well as asymptomatic individuals infected with the virus, are specific to gp120 and gp160. Occasionally these antibodies are neutralizing. The envelope glycoproteins are the HIV-1 antigen most consistently recognized by antibodies in AIDS and ARC patient sera. Allan et al., "Major Glycoprotein Antigens that Induce Antibodies in AIDS Patients are Encoded by HTLV-III," Science, 228:1091–1094 (1985); and Barin et al., "Virus Envelope Protein of HTLV-III Represents Major Target Antigen for Antibodies in AIDS Patients," Science, 228:1094–1096 (1985). In addition, antibodies in patient sera also recognize epitopes of the viral core proteins encoded by the gag gene.

Immunologically important HIV-1 antigens for use in diagnosis and as potential vaccine compositions have been prepared by cloning portions of the HIV-1 genome in various expression systems such as bacteria, yeast or vaccinia. Cabradilla et al., "Serodiagnosis of Antibodies to the Human AIDS Retrovirus With a Bacterially Synthesized env Polypeptide," Biotechnology, 4:128–133 (1986); and Chang et al., "Detection of Antibodies to Human T-Cell Lymphotropic Virus-III (HTLV-III) With an Immunoassay Employing a Recombinant *Escherichia coli*—Derived Viral Antigenic Peptide," Biotechnology, 3:905–909 (1985). HIV-1 antigens produced by recombinant DNA methods, however, must still be exhaustively purified to avoid adverse reactions upon vaccination and false positive reactions in ELISA assays due to any antibody reactivity to antigens of the expression system which may contaminate the HIV-1 antigen preparation. Also, denaturation of HIV-1 antigens during purification may destroy important antigen activity. Preparation of proteins from intact viruses can also result in contamination by intact virus.

Several publications have presented data showing immunologic reactivity of selected synthetic peptides corresponding to antigenic proteins of HIV-1. In one study, a peptide having the amino acid sequence Tyr-Asp-Arg-Pro-Glu-Gly-Ile-Glu-Glu-Gly-Gly-Glu-Arg-Asp-Arg-Asp-Arg-Ser-Gly-Cys which corresponds to amino acid residues 735–752 of HIV-1 was synthesized. Kennedy et al., "Antiserum to a Synthetic Peptide Recognizes the HTLV-III Envelope Glycoprotein," Science, 231:1556–1559 (1986). This peptide, derived from a portion of gp41, was used to immunize rabbits in an attempt to elicit a neutralizing antibody response to HIV-1. Furthermore, several sera from AIDS patients known to contain anti-gp41 antibodies were weakly reactive with this peptide, thus indicating that this peptide contains at least one epitope recognized, to some extent, by antibodies to native gp160/gp41. However, this peptide has not been shown to elicit neutralizing antibodies in mammals other than rabbits nor has it been suggested for use as a human vaccine.

In antigenic proteins of HIV-1 there are antigenic epitopes recognized by antibodies, cytotoxic T cells, helper T cells and also in antibody-dependent cellular cytotoxicity (ADCC). Traditionally, neutralizing antibodies are considered as essential in preventing viral infection. A neutralizing antibody binds to an infectious virus particle and in this process the infectivity of the virus particle is destroyed.

Cellular mechanisms for elimination of virus infected cells involve cytotoxic T cells, T-helper cells and ADCC. The epitopes involved in neutralization and in the various cellular immune mechanisms need not necessarily be the same.

Previously it has been found that ADCC is an immunological defense mechanism that operates in viral infections. In this reaction, antigen-specific antibodies will bind to surface structures on the target cell and thus induce killing mediated by major histocompatibility complex (MHC)-unrestricted CD16+, Fc receptor-bearing effector cells. HIV specific cytotoxicity in the peripheral blood of most seropositive individuals is also mediated by MHC-unrestricted ADCC effector cells which are armed with env-specific IgG antibodies, Tyler et al. J. Immunol., 142:1177 (1989); Tanneau et al. J. Infect Dis., 162:837 (1990); Riviere et al. J. Virol., 63:2270 (1989). HIV-specific ADCC activity has been found in the majority of sera from HIV-1 infected individuals, Ljunggren et al. J. Immunol., 139:2263 (1987), Lyerly et al., AIDS Res. Hum. Retroviruses 3:409 (1987). Both type and strain specific ADCC have been observed and antibodies in some sera mediated ADCC against all strains whereas other sera lacked ADCC activity completely, Ljunggren et al., J. Virol. 63:3376 (1989). In pediatric HIV-1 infection, presence of ADCC-mediating antibodies correlates significantly with a better clinical stage, Ljunggren et al., J. Infect. Dis. 161:198 (1990). The ADCC reaction appears early after HIV-infection and broadly reacting ADCC against HIV-1$_{HTLVIIIB}$ infected target cells appears between 2 and 12 months after seroconversion.

Activated cells expressing HIV antigens on their surface are possible targets for ADCC. HIV-infected autologous CD4+ T-cell blasts have recently been shown to serve as targets for lysis by ADCC, Tanneau et al. J. Infect Dis., 162:837 (1990). The envelope glycoproteins of HIV have been suggested as target epitopes in a number of studies. Evans et al. AIDS, 3:273 (1989) used affinity purified human Ig or polyclonal rabbit sera against env proteins of HIV-1 and found antibodies mediating ADCC against gp120 and gp41. Koup et al. J Virol, 63:584 (1989), have used vaccinia virus vectors expressing envelope glycoproteins (gp160, gp120 and gp41) or gag proteins (p55, p40, p24 and p17) in lymphoblastoid cell lines. Only the envelope glycoprotein complex gp120/gp41 was found to be the target antigen for HIV-specific ADCC which was also confirmed in another study using a similar system, Tanneau et al. J. Infect Dis., 162:837 (1990).

More defined regions have also been demonstrated in a number of studies. A murine monoclonal antibody directed to the V3 region (a.a. 309–318) of gp120 mediated both neutralization, titer 1:500, and ADCC, titer 1:800, against HTLVIIIB. Broliden et al., J. Virol., 64:936 (1990). Also, a chimeric mouse-human antibody directed against the V3 region (a.a. 308–322) induced ADCC as well as neutralization and fusion inhibition, Liou et al. J. Immunol, 143:3967 (1989). Lyerly et al., AIDS Res Hum Retroviruses, 3:409 (1987), have localized an ADCC epitope in the C-terminal part of gp120 (a.a.467–511).

SUMMARY OF THE INVENTION

In accordance with the present invention, novel peptides corresponding to epitopes of HIV-1 gp120 protein are disclosed and described. Each peptide comprises an epitopic amino acid sequence from human immunodeficiency virus gp120 protein, wherein the epitope is located within SEQ ID NO:1, SEQ ID NO:5, SEQ ID NO:6, SEQ ID NO:7, SEQ ID NO:8, SEQ ID NO:12, SEQ ID NO:14, SEQ ID NO:19, SEQ ID NO:20, SEQ ID NO:21, SEQ ID NO:36 or SEQ ID NO:41, and wherein antisera raised in monkeys against the epitopic sequence has a specific antibody-dependent cellular cytotoxicity index value greater than 0.5 at a dilution greater than 1:30.

In another embodiment of the present invention, each peptide has an epitopic sequence having an amino acid sequence that consists essentially of a sequence selected from the group consisting of SEQ ID NO:1, SEQ ID NO:5, SEQ ID NO:6, SEQ ID NO:7, SEQ ID NO:8, SEQ ID NO:12, SEQ ID NO:14, SEQ ID NO:19, SEQ ID NO:20, SEQ ID NO:21, SEQ ID NO:36 or SEQ ID NO:41.

In accordance with another aspect of the present invention, the novel peptides are used to formulate a vaccine composition. The vaccine composition comprises an epitopic amino acid sequence from human immunodeficiency virus gp120 protein, wherein the epitope is located within SEQ ID NO:1, SEQ ID NO:5, SEQ ID NO:6, SEQ ID NO:7, SEQ ID NO:8, SEQ ID NO:12, SEQ ID NO:14, SEQ ID NO:19, SEQ ID NO:20, SEQ ID NO:21, SEQ ID NO:36 or SEQ ID NO:41, and wherein antisera raised in monkeys against the epitopic sequence has a specific antibody-dependent cellular cytotoxicity index value greater than 0.5 at a dilution greater than 1:30, in an amount effective to induce an immune response in a mammal together with a pharmaceutically acceptable carrier. In a preferred embodiment, the vaccine composition further comprises an adjuvant such as Freund's complete adjuvant, Freund's incomplete adjuvant, muramyl dipeptide, levamisole, isoprinosine or tuftsin.

In accordance with yet another aspect of the present invention, at least two of the novel peptides are used in the vaccine composition. Each peptide comprises an epitopic amino acid sequence from human immunodeficiency virus gp120 protein, wherein the epitope is located within SEQ ID NO:1, SEQ ID NO:5, SEQ ID NO:6, SEQ ID No:7, SEQ ID NO:8, SEQ ID NO:12, SEQ ID NO:14, SEQ ID NO:19, SEQ ID NO:20, SEQ ID NO:21, SEQ ID NO:36 or SEQ ID NO:41, and wherein antisera raised in monkeys against the epitopic sequence has a specific antibody-dependent cellular cytotoxicity index value greater than 0.5 at a dilution greater than 1:30. The peptides are present in an amount effective to induce an immune response in a mammal, and are combined with a pharmaceutically acceptable carrier.

In a preferred embodiment, this vaccine composition further comprises an adjuvant, such as Freund's complete adjuvant, Freund's incomplete adjuvant, muramyl dipeptide, levamisole, isoprinosine and tuftsin.

In accordance with yet another aspect of the present invention, there is disclosed a method of protecting a mammal from infection with human immunodeficiency virus, comprising administering to the mammal one of the vaccine compositions described herein. The administration can be by intravenous, intramuscular, subcutaneous, or intraperitoneal injection.

In accordance with still another aspect of the present invention, there is disclosed a method for inducing neutralizing anti-HIV antibodies in a mammal, comprising the step of administering an effective antibody-inducing amount of a composition comprising an epitopic amino acid sequence from human immunodeficiency virus gp120 protein, wherein the epitope is located within SEQ ID NO:1, SEQ ID NO:5, SEQ ID NO:6, SEQ ID NO:7, SEQ ID NO:8, SEQ ID NO:12, SEQ ID NO:14, SEQ ID NO:19, SEQ ID NO:20, SEQ ID NO:21, SEQ ID NO:36 or SEQ ID NO:41, and wherein antisera raised in monkeys against the epitopic sequence has a specific antibody-dependent cellular cytotoxicity index value greater than 0.5 at a dilution greater than 1:30, in an amount effective to induce an immune response in a mammal together with a pharmaceutically acceptable carrier.

In another embodiment of the invention, the vaccine composition comprises at least two of the novel peptides. Each peptide comprises an epitopic amino acid sequence from human immunodeficiency virus gp120 protein, wherein the epitope is located within SEQ ID NO:1, SEQ ID NO:5, SEQ ID NO:6, SEQ ID NO:7, SEQ ID NO:8, SEQ ID NO:12, SEQ ID NO:14, SEQ ID NO:19, SEQ ID NO:20, SEQ ID NO:21, SEQ ID NO:36 or SEQ ID NO:41, and wherein antisera raised in monkeys against the epitopic sequence has a specific antibody-dependent cellular cytotoxicity index value greater than 0.5 at a dilution greater than 1:30. The peptides are present in an amount effective to induce an immune response in a mammal, and are combined with a pharmaceutically acceptable carrier.

DETAILED DESCRIPTION OF THE INVENTION

The present invention provides peptides which have been found to elicit production of HIV neutralizing antibodies by primate subjects. The peptides correspond to regions of the gp120 protein with coordinates as defined by Kennedy et al. The peptides of the present invention are termed gp120-12 (amino acid coordinates 159–183), gp120-15 (amino acid coordinates 200–225), gp120-16 (amino acid coordinates 213–237) and gp120-19 (amino acid coordinates 255–276). Although peptide gp120-19 is similar to a peptide that has been described (Ho et al., Science, 239:1021–1023 (1988)), it has now been found that gp120-19 elicits neutralizing antibodies in primates. The peptides of the present invention can be used as immunogens in vaccine compositions and to elicit polyclonal or monoclonal antibody production; particularly important are HIV neutralizing antibodies.

Proteins contain a number of antigenic determinants or epitopes which are the regions of the proteins comprising the recognition and binding sites for specific antibodies. In general, proteins contain between 5 to 10 epitopes, each of which contains a sequence of 6 to 8 amino acids. Epitopes can be either continuous, in which the 6 to 8 amino acids are present in linear sequence, or discontinuous, in which the amino acids that form the epitope are brought together by the three dimensional folding of the protein. Even though an epitope constitutes only a relatively few amino acids, its reactivity with an antibody may be influenced by the amino acids in the protein which surround the epitope.

Studies aimed at mapping antigenic sites or epitopes of proteins have been aided by the use of synthetic peptides corresponding to various regions of the proteins of interest. Lerner et al., in, The Biology of Immunological Disease: A Hospital Practice Book, (Dixon and Fisher, eds.) pp. 331–338 (1983); and Lerner, Adv. Immunol., 36:1 (1984). In addition to their usefulness in epitope mapping studies, synthetic peptides, if encompassing major antigenic determinants of a protein, have potential as vaccines and diagnostic reagents. Van Regenmortel, Ann. Inst. Pasteur/Virol 137E:497–528 (1986); and Van Regenmortel, Laboratory Techniques in Biochemistry and Molecular Biology, Buroden and Van Knippenburg eds. Vol. 19, synthetic Peptides as Antigens, Elsevier ISBN 0-444-80974-0 (1988).

Synthetic peptides have several advantages with regard to specific antibody production and reactivity. The exact sequence of the synthesized peptide can be selected from the amino acid sequence of the protein as determined by amino acid sequencing of the protein or the predicted amino acid sequence determined from the DNA sequence encoding the protein. The use of specific synthetic peptides eliminates the need for the full-length protein in vaccination and the production of or assay for antibodies. Furthermore, the solid phase peptide synthetic techniques of Merrifield and coworkers allow for essentially unlimited quantities of the synthesized peptide of interest to be chemically produced. Erickson and Merrifield in The Proteins, 3rd Edit., Vol. 2, Academic Press, New York, Chapter 3 (1976). The availability of automated peptide synthesizers has further advanced such techniques.

Although a variety of criteria can be used to predict antigenic regions of proteins, peptides corresponding to such regions may not always be useful as vaccines. For example, antigenicity may be lost because the peptide is not in the proper spatial orientation to be recognized by antibodies which react with the protein. It has also been found that certain peptides derived from type C retroviruses and HIV act as immune-suppressive agents much as HIV itself. Cianciolo et al., J. Immunol., 124:2900–2905 (1980); and Cianciolo et al., Science, 230:453–455 (1985). Peptides such as these, which have a deleterious effect on the patient, would not be suitable for use as vaccines.

Furthermore, as is particularly evident with HIV-1 and HIV-2, there is significant genetic variability within each of these two virus groups leading to many serotypes, or isolates, of the viruses. This has put a significant constraint on choosing a region of a protein from which to derive a peptide for use in formulating immunogens. However, certain immunodominant portions of HIV-1 and HIV-2 proteins have been found to be relatively invariant. Synthetic peptides may also be key to viral vaccines in that they may induce an immune response against type common sequences not normally immunogenic in the native molecule. These otherwise silent epitopes may be of broad protective specificity. Steward et al., Immunol. Today, 8:51–58 (1987). Several experimental vaccines have been formulated with the aim of preventing infection in those people who are likely to be exposed to the virus. Berman et al., "Protection of Chimpanzees from Infection by HIV-2 After Vaccination With Recombinant Glycoprotein gp120 but Not gp160," Nature, 345:622–625 (1990). Synthetic peptides corresponding to regions of immunologically important proteins of HIV have now found immediate use in diagnostic methods for detection of HIV, as potential vaccines for HIV and for the production of polyclonal and monoclonal antibodies.

A number of neutralization epitopes on gp120 have been found and defined by several investigators, for an overview see Bolognesi, AIDS (1989) 3(suppl 1):S111–s118. In this overview Bolognesi refers to four different virus neutralization epitopes with the following amino acid coordinates: 254–274, 303–337, 458–484 and 491–523. The peptide with amino acid coordinates 254–274 was used to immunize rabbits and the resulting antiserum was found to neutralize HIV-1 as described above. Ho et al.

The peptides encompassed by the invention comprise amino acid sequences each containing at least one continuous (linear) epitope that elicits production of HIV specific antibodies in the immunized host.

The invention thus encompasses immunogenic peptides corresponding to regions of HIV gp120 protein encoded by the envelope gene of HIV-1 HTLV III-B described by Muesing et al., "Nucleic Acid Structure and Expression of the Human AIDS/Lymphadenopathy retrovirus," Nature, 313:450–458 (1985). The nucleotide sequence is given in Genbank Release 63 under the name HIVPV22. The invention further encompasses functionally equivalent variants of the peptides which do not significantly affect the immunogenic properties of the peptides. For instance, conservative substitution of amino acid residues, one or a few amino acid residues by amino acid analogues are within the scope of the invention.

Homologs are peptides which have conservatively substituted amino acid residues. Amino acids which can be conservatively substituted for one another include but are not limited to: glycine/alanine; valine/isoleucine/leucine; asparagine/glutamine; aspartic acid/glutamic acid; serine/threonine; ysine/arginine; and phenylalanine/tyrosine. Homologous peptides are considered to be within the scope of the invention if they are recognized by antibodies which recognize the peptides designated gp120-12, gp120-15, gp120-16 and gp120-19, the sequences of which are shown below. Further, all homologous peptides corresponding to the peptides of the present invention but derived from different HIV isolates are also encompassed by the scope of this invention.

Analogues are defined as peptides which are functionally equivalent to the peptides of the present invention but which contain certain non-naturally occurring or modified amino acid residues. Additionally, polymers of one or more of the peptides, and peptide analogues or homologs are within the scope of the invention. Also within the scope of this invention are peptides of fewer amino acid residues than gp120-12, gp120-15, gp120-16 and gp120-19, respectively, but which encompass one or more immunogenic epitopes present in any one of the peptides and thus retain the immunogenic properties of the base peptide. Analytical techniques for determining the extent to which the peptides in question can be shortened at either end, while still retaining the immunogenic epitope of the longer sequence, are described below.

Addition of amino acids to either end of the peptides specifically disclosed herein is also considered within the scope of the present invention, so long as such addition does not significantly deleteriously affect the immunological properties of that peptide. Routine testing can determine whether the desired immunological properties are retained by such supplemented or truncated peptides. If amino acids are added, it is preferred that the resulting peptides are still relatively short, e.g., not more than about 50 amino acids long, preferably not more than about 40 or 45 amino acids long, and most preferably not more than about 25, 30, or 35 amino acids in length.

The peptides of the present invention were synthesized by known solid phase peptide synthesis techniques. Barany and Merrifield, The Peptides: Analysis, synthesis, Biology, Vol. 1, Gross and Meinenhofer, eds., Academic Press, New York, Chap. 1 (1980). The synthesis also allows for one or more amino acids not corresponding to the original protein sequence to be added to the amino or carboxyl terminus of the peptide. Such extra amino acids are useful for coupling the peptides to another peptide, to a large carrier protein or to a solid support. Amino acids that are useful for these purposes include but are not limited to tyrosine, lysine, glutamic acid, aspartic acid, cysteine and derivatives thereof. Additional protein modification techniques may be used, e.g., $NH_2$-acetylation or COOH-terminal amidation, to provide additional means for coupling the peptides to another protein or peptide molecule or to a support. Procedures for coupling peptides to each other, carrier proteins and solid supports are well known in the art. Peptides containing the above-mentioned extra amino acid residues either carboxy or amino terminally, uncoupled or coupled to a carrier or solid support are consequently within the scope of the invention. Reference to the peptides of the present invention encompasses all of the embodiments discussed herein.

An alternative method of vaccine production is to use molecular biology techniques to produce a fusion protein containing one or more of the peptides of the present invention and a highly immunogenic protein. For instance, fusion proteins containing the antigen of interest and the B subunit of cholera toxin have been shown to induce an immune response to the antigen of interest. See Sanchez et al., "Recombinant System for Overexpression of Cholera Toxin B Submit In Vibrio cholerae as a Basis for Vaccine Development," Proc. Natl. Acad. Sci. U.S.A., 86:481–485 (1989). Such chimeric peptides may be orally administered.

The novel peptide sequences are set forth below. The amino acid residues are derived from the nucleotide sequence previously described by Muesing et al., "Nucleic Acid Structure and Express of the Human AIDS/Lymphadenopathy Retrovirus," Nature, 313:450–458 (1985). It is preferred that the peptides possess an amido group at their carboxy termini rather than a carboxyl group. The carboxy terminus can also be a carboxyl group as well as a moiety described below.

gp120-12

X—Gly—Glu—Ile—Lys—Asn—Cys—Ser—Phe—Asn—Ile—Ser—Thr—Ser—Ile—
Arg—Gly—Lys—Val—Gln—Lys—Glu—Tyr—Ala—Phe—Phe—Y—Z gp120-15

X—Leu—Thr—Ser—Cyc—Asn—Thr—Ser—Val—Ile—Thr—Gln—Ala—Cys—Pro—
Lys—Val—Ser—Phe —Glu—Pro—Ile—Pro—Ile—His—Tyr—Cys—Y—Z gp120-16

X—Pro—Lys—Val—Ser—Phe—Glu—Pro—Ile—Pro—Ile—His—Tyr—Cys—Ala—
Pro—Ala—Gly—Phe—Ala—Ile—Leu—Lys—Cys—Asn—Asn—Y—Z gp120–19

X—Thr—His—Gly—Ile—Arg—Pro—Val—Val—Ser—Thr—gln—Leu—Leu—Leu—
Asn—Gly—Ser—Leu—Ala—Glu—Glu—Y—Z wherein X is either a hydrogen atom of the amino terminal $NH_2$ group of the peptide or an additional amino acid being selected to facilitate coupling of the peptide to a carrier; Y is absent or Cys; and Z is the carboxyl group of the carboxy terminal amino acid or an amido group. The amino acid abbreviations used are defined in Table 2.

The peptides are useful as vaccines to protect against future infection by HIV or to heighten the immune response to HIV in subjects already infected by HIV. Although any primate or preferably human subject could be vaccinated with the peptides, the most suitable subjects are people at risk for HIV infection. Such subjects include but are not limited to homosexuals, prostitutes, intravenous drug users and those in the medical professions who have contact with patients or biological samples. The invention also provides monoclonal and polyclonal antibodies which specifically recognize the peptides. The invention further provides antibodies which neutralize HIV.

In the preferred embodiment of the present invention, the peptides are formulated into compositions for use as immunogens. These immunogens can be used as vaccines in mammals including primates and humans or to elicit production of polyclonal and monoclonal antibodies in animals, For formulation of such compositions, an immunogenically effective amount of at least one of the peptides is admixed with a physiologically acceptable carrier suitable for administration to mammals including humans. The peptides may be covalently attached to each other, to other peptides, to a protein carrier or to other carriers, incorporated into liposomes or other such vesicles, and/or mixed with an adjuvant or adsorbent as is known in the vaccine art. For instance, the peptide or peptides can be mixed with immunostimulating complexes as described by Takahashi et al., "Induction of CD8+ Cytotoxic T Cells by Immunization With Purified HIV-1 Envelope Protein and ISCOMS," Nature, 344:873–875 (1990). Alternatively, the peptides are uncoupled and merely admixed with a physiologically acceptable carrier such as normal saline or a buffering compound suitable for administration to mammals including humans.

The immune response to the peptides of the present invention can be enhanced by a wide variety of agents. The list of available adjuvants is long and is rapidly growing. In a preferred embodiment, Freund's complete adjuvant is used to increase the immune response of the mammal receiving the peptide as a vaccine.

As with all immunogenic compositions for eliciting antibodies, the immunogenically effective amounts of the peptides of the invention must be determined empirically. Factors to be considered include the immunogenicity of the native peptide, whether or not the peptide will be complexed with or covalently attached to an adjuvant or carrier protein or other carrier and route of administration for the composition, i.e. intravenous, intramuscular, subcutaneous, etc., and the number of immunizing doses to be administered. Such factors are known in the vaccine art and it is well within the skill of immunologists to make such determinations without undue experimentation.

The invention is further illustrated by the following specific examples which are not intended in any way to limit the scope of the invention.

EXAMPLE 1

Peptide Synthesis

An Applied Biosystems peptide-synthesizer Model 430 A, was utilized for the synthesis of the peptides of the present invention. Each synthesis used a p-methylbenzyl-hydrylamine solid phase support resin (Peptides International, Louisville, Ky.). The peptides were synthesized according to the Users Manual for Peptide Synthesizer Model 430A, Applied Biosystems, 1986.

All amino acids for use in synthesis contained t-butylcarbonyl groups (t-Boc) protecting the α-NH$_2$ group and were obtained from Novabiochem AG, Switzerland. Amino acids with reactive side chain groups contained additional protective groups to prevent unwanted and undesirable side chain reactions. The individual protected amino acids used in synthesizing all of the peptides are set forth in Table 1.

Table 1
Amino Acids Used in Peptides Synthesis
Boc-Ala-OH
Boc-Arg (Tos)-OH
Boc-Asn-OH
Boc-Asp (Obzl)-OH
Boc-Cys (Pmeobzl)-Oh
Boc-Glu (Obzl)-OH
Boc-Gln-OH
Boc-Gly-OH
Boc-His-(Tos)-OH
Boc-Ile-OH^1/2 H$_2$O
Box-Leu-OH^H$_2$O
Box-Lys (2-CI-Z)-OH (cryst.)
Box-Met-OH
Boc-Phe-OH
Boc-Pro-OH
Boc-Ser (Bzl)-OH^DCHA
Boc-Thr (bzl)-OH
Boc-Trp (Formyl)-OH
Boc-Tyr (2-Br-Z)-OH
Boc-Val-OH
Tos: Tosyl or p-Toluene sulfonic acid
   Obzl=Benzyloxy
   Pmeobzl=p-Methylbenzyloxy
   2-CL-Z=Carbobenzoxy chloride
   2-Br-Z=Carbobenzoxy bromide After completion of a particular synthesis, the protecting groups were removed from the synthesized peptide and the peptide was cleaved from the solid support resin by treatment with Trifluoromethane Sulfonic Acid (TFMSA) according to the method described by Bergot et al., "Utility of Trifluoromethane Sulfonic Acid as a Cleavage Reagent in Solid Phase Peptide Synthesis," Applied Biosystems User Bulletin, Peptide Synthesizer, Issue No. 16, Sep. 2, 1986. The following is the detailed protocol used.

1. For 1 gram peptide-resin, 3 ml Thio-Anisol 1,2-Ethane-Dithiol (2:1) was added as scavenging agent and the mixture was incubated with continuous stirring for 10 min. at room temperature.

2. Trifluoracetic Acid (TFA), 10 ml, was added and stirred continuously for 10 min. at room temperature.

3. TFMSA, 1 ml, was added dropwise with forceful stirring and reacted for 25 min. at room temperature.

4. Following cleavage, the peptides were precipitated with and washed with anhydrous ether.

5. The precipitated and washed peptides were dissolved in a small volume of TFA (approximately 5 ml).

6. The dissolved peptides were again precipitated and washed as above in step 4 and the precipitate was dried under a stream of N$_2$.

Prior to use in specific assays, the peptides can be further purified, if desired, by reverse phase high performance liquid chromatography (HPLC). A particularly suitable column for such purification is the reverse-phase Vydak™ C-18 column using a water (TFA)—acetonitrile (TFA) gradient to elute the peptides. Forty peptides covering the entire sequence of HIV-1 gp120 were synthesized having the amino acid sequences shown in Table 2. A truncated peptide gp120-16/B with the amino acid coordinates 213–224 was also synthesized.

TABLE 2

| Peptide | Amino Acid Coordinates* | Amino Acid Sequence** | SEQ. I.D. No. |
|---|---|---|---|
| gp120-1 | 1–28 | MRVKEKYQHLWRWGWRWGTMLLCMLMIC | 1 |
| gp120-2 | 23–46 | GKIGNMRQAHCNISRAKWNNTLK | 2 |
| gp120-3 | 41–64 | GVPVWKEATTTLFCASDAKAYDTE | 3 |
| gp120-4 | 54–74 | CASDAKAYDTEVHNVWATHAC | 4 |
| gp120-5 | 65–89 | VHNVWATHACVPTDPNPQEVVLVNV | 5 |
| gp120-6 | 75–100 | VPTDPNPQEVVLVNVTENFNMWKNDM | 6 |
| gp120-7 | 90–116 | TENFNMWKNDMVEQMHEDIISLWDQSL | 7 |
| gp120-8 | 101–126 | VEQMHEDIISLWDQSLKPCVKLTPLC | 8 |
| gp120-9 | 117–141 | KPCVKLTPLCVSLKCTDLKNDTNTN | 9 |
| gp120-10 | 127–151 | VSLKCTDLKNDTNTNSSSGRMIMEK | 10 |
| gp120-11 | 169–192 | SSSGRMIMEKGEIKNCSFNISTS | 11 |
| gp120-12 | 152–176 | GEIKNCSFNISTSIRGKVQKEYAFF | 12 |
| gp120-13 | 165–192 | IRGKVQKEYAFFYKLDIIPIDNDTTSYT | 13 |
| gp120-14 | 177–205 | YKLDIIPIDNDTTSYTLTSCNTSVITQAC | 14 |
| gp120-15 | 193–218 | LTSCNTSVITQACPKVSFEPIPIHYC | 15 |
| gp120-16 | 206–230 | PKVSFEPIPIHYCAPAGFAILKCNN | 16 |
| gp120-16/B | 213–224 | IPIHYCAPAGFA | 41 |
| gp120-17 | 219–237 | APAGHAILKCNNKTFNGTGPCTNVSTVQC | 17 |
| gp120-18 | 231–257 | KTFNGTGPCTNVSTVQCTHGIRPVVST | 18 |
| gp120-19 | 248–269 | THGIRPVVSTQLLLNGSLAEEE | 19 |
| gp120-20 | 258–282 | QLLLNGSLAEEEVVIRSANFTDNAK | 20 |
| gp120-21 | 270–295 | VVIRSANFTDNAKTIIVQLNQSVEIN | 21 |
| gp120-22 | 283–306 | TIIVQLNQSVEINCTRPNNNTRKS | 22 |
| gp120-23 | 296–320 | CTRPNNNTRKSIRIQRGPGRAFVTI | 23 |
| gp120-24 | 307–330 | IRIQRGPGRAFVTIGKIGNMRQAH | 24 |
| gp120-25 | 321–343 | GKIGNMRQAHCNISRAKWNNTLK | 25 |
| gp120-26 | 331–353 | CNISRAKWNNTLKQIDSKLREQF | 26 |
| gp120-27 | 344–366 | QIDSKLREQFGNNKTIIFKQSSG | 27 |
| gp120-28 | 354–377 | GNNKTIIFKQSSGGDPEIVTHSFN | 28 |
| gp120-29 | 367–389 | GDPEIVTHSFNCGGEFFYCNSTQ | 29 |
| gp120-30 | 378–400 | CGGEFFYCNSTQLFNSTWFNSTW | 30 |
| gp120-31 | 390–409 | LFNSTWFNSTWSTEGSNNTE | 31 |
| gp120-32 | 401–417 | STEGSNNTEGSDTITLP | 32 |
| gp120-33 | 410–429 | GSDTITLPCRIKQFINMWQE | 33 |
| gp120-34 | 418–444 | CRIKQFINMWQEVGKAMYAPPISGQIR | 34 |
| gp120-35 | 430–453 | VGKAMYAPPISGQIRCSSNITGLL | 35 |
| gp120-36 | 445–466 | CSSNITGLLLTRDGGNNNNESE | 36 |
| gp120-37 | 454–476 | LTRDGGNNNNESEIFRPGGGDMR | 37 |
| gp120-38 | 467–488 | IFRPGGGDMRDNWRSELYKYKV | 38 |
| gp120-39 | 477–447 | DNWRSELYKYKVVKIEPLGVA | 39 |
| gp120-40 | 489–511 | VKIEPLGVAPTKAKRRVVQREKR | 40 |

**Amino acid abbreviations

| | | |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

*As previously described by Muesing et al.

EXAMPLE 2

Cells and Virus Stocks

All neutralization tests were performed using H-9 cells and HTLV-111B virus (originating from R. C. Gallo and supplied by Dr. William Hall, North Shore Hospital, Manhasset, N.Y.). H-9 cells (designated H9 NY) were maintained in RPMI Medium (Gibco) supplemented with 20% fetal calf serum (FCS), penicillin/streptomycin (PEN/STREP 50 μg/ml each and without any fungicides). Cells were subcultured at a dilution of 1:3 every 4 days.

Cells were scraped from the plates and pelleted by centrifugation at 325×g. Pelleted cells were resuspended in 1 ml of stock virus previously diluted 1/10 and allowed to adsorb for 60 min at 37° C. with frequent stirring. After adsorption of the virus, the cells were recentrifuged and resuspended in 10 ml of RPMI with 20% FCS and polybrene (2 μg/ml) (giving a final concentration of 5×10⁵ cells/ml) and incubated at 37° C. in 5% $CO_2$.

Infected cells were shown to be detectable at 4–5 days post-infection (p.i.) by monitoring syncytia formation, positive cells in immunofluorescence and p-24 production (assayed by the Abbott p-24 antigen test). The peak of HIV production was seen 10–15 days p.i. at which time virus was collected. After low speed centrifugation to remove debris, supernatants containing virus collected from infected cells were frozen in stocks at −90° C. One virus stock with endpoint titer of 40,000 50% tissue culture infective doses ($TCID_{50}$) was used throughout the studies (referred to as NT3-NT19).

EXAMPLE 3

Preparation of Peptides for Immunization

Peptides according to the present invention were covalently coupled to ovalbumin grade V (Sigma, St. Louis, Mos., U.S.A.) at an approximate 10:1 (peptide:ovalbumin) molar ratio using N-succinimidyl 3-(2-pyridyldithio) propionate (SPDP), (Pharmacia, Uppsala, Sweden) as bifunctional linker according to the manufacturer's instructions (Pharmacia) i.e., briefly as follows:

Ovalbumin was dissolved in coupling buffer (0. 2M $NaH_2PO_4$, pH 8.5). The dissolved ovalbumin was then run through a Sephadex G-25M column (Pharmacia, Sweden), using the same buffer. Protein concentration was measured at 280 nm and the recovery was determined. SPDP was dissolved in 99.5% ethanol to a final concentration of 40 nM. SPDP was then added dropwise to the ovalbumin solution under stirring. The SPDP-ovalbumin mixture was then left at room temperature for approximately 30 minutes. The ovalbumin-SPDP conjugate was separated from unconjugated SPDP by running the mixture through a Sephadex G-25M column, using water as eluent. The degree of substitution for the ovalbumin-SPDP conjugate was determined after diluting 50 μl conjugate in 2 ml of water, by measuring the diluted conjugate at 280 nm and the diluted conjugate plus 100 μl Dithiothreitol (DDT) (Sigma) at 343 nm, in order to determine the amount to be added to the peptide solution.

Finally, the synthetic peptide to be coupled to the ovalbumin-SPDP conjugate was dissolved in 10% acetic acid to a final concentration of 1 mg/ml and a suitable amount of ovalbumin-SPDP conjugate (as determined by the substitution degree above) was added and allowed to stand overnight at room temperature.

EXAMPLE 4

Immunization Protocols

*Maccaca fascicularis* were used to generate antibodies. Prior to the initial peptide injection, a blood sample was drawn from the monkeys. This initial blood sample is termed "pre-immune" (Tables 3–6) and is used as an internal control and analyzed simultaneously with respective immune serum.

The monkeys were injected with 100 μg peptide-SPDP-ovalbumin suspended in 0.5 ml phosphate buffered saline (PBS) The monkeys were immunized intramuscularly three times, three weeks apart. As adjuvant, 0.5 ml of Freund's complete adjuvant was used for all immunizations. Two weeks after the final immunization, the monkeys were bled and pre-immune and hyperimmune sera were subject to neutralization assays as described in Example 5.

EXAMPLE 5

HIV-1 Neutralization Assay

Sera containing antibodies that neutralize HTLV 11-B infectivity were detected by their ability to prevent HIV-1 syncytium formation, p-24 antigen production and decreased number of infected cells as determined by immuno-fluorescence markers, compared to control infections lacking peptide specific antisera. Stock virus, described in Example 2 was diluted to 100 $TCID_{50}$ and mixed with serial fourfold dilutions (1/5, 1/20, and 1/80) of complement-inactivated immune sera obtained from the monkeys immunized as described in Example 4. As a positive control, a guinea pig hyperimmune serum (referred to as MSV) with known HIV neutralizing titer of 1/40–1/160 was included in all experiments (kindly provided by Prof. B. Morein, Dept. Veterinary Virology, BMC, Uppsala, Sweden). After incubation for 60 min at 37° C. or 16 hours at 4° C., the serum-virus mixture was added to 1×10⁶ H-9 cells and incubated for another 60 min at 37° C. Following incubation, the cells were washed once and placed in 24 well multidish plates with 2 ml of growth medium (RPMI, 10%, FCS, 2 μg polybrene/ml) per well.

Cells were examined under the microscope (magnification×200) for the presence of syncytia on days 5–12 p.i. Supernatants from infected cells were assayed for the presence of p-24 antigen according to the manufacturer's instructions (Abbott ag test HIVAG-1®, Enzyme Immunoassay for the Detection of Human Immunodeficiency Virus Type I (HIV-1) Antigen(s) in Human Serum or Plasma) in tenfold serial dilutions (1/10–1/1,000) at 10 days p.i. The results are presented as absorbance values at 454 nm with higher absorbance values indicating higher protein concentration and hence HIV infection. Serial dilutions of the supernatants were made so as to detect p-24 concentrations in the most accurate range (<2.0 absorbance units).

The number of infected cells were determined at the end of the experiment (usually on day 15 p.i.) by acetone-fixation of cells on slides adopted for immunofluorescence (IF). An indirect IF test was used according to standard procedures described in Jeansson et al., "Elimination of Mycoplasmas from Cell Cultures Utilizing Hyperimmune Sera", Ex. Cell Res., 161:181–188 (1985), with 1/400 dilution hyperimmune sera from HIV-infected individuals and a fluorescein isothiocyanate (FITC) labeled antihuman IgG antibody (Bio-Merieux France) diluted 1/100. Tables 3–6 show the results obtained from screening of hyperimmune sera from monkeys immunized with peptides 1–40.

In Tables 3(A-D)-6 the p24 antigen content of the supernatants was analyzed by ELISA as described above. The relative amount of antigen positive cells is depicted as AG POS cells wherein the percentages are represented by: −=0%, +=>0–2%, ++=3–10% and +++=11–20% where the percentage interval indicates the number of antigen positive cells.

Table 3A (HIVNT3P1.XLS) depicts the results obtained with sera derived from monkeys immunized with peptides gp120-1–gp120-10. The cells used were H9 NY and the virus used was HTLV-IIIB, Batch 18 described in Example 2. The incubation protocol was (virus plus serum) incubation at 37° C. for one hour.

Table 3B (HIVNT4P1.XLS) depicts the results obtained with sera derived from monkeys immunized with peptides gp120-11–gp120-20. The cells used were H9 NY and the virus used was HTLV-IIIB, Batch 18 described in Example 2. The incubation protocol was (virus plus serum) incubation at 37° C. for one hour.

Table 3C (HIVNT5P1.XLS) depicts the results obtained with sera derived from monkeys immunized with peptides gp120-21–gp120-30. The cells used were H9 NY and the virus used was HTLV-IIIB, Batch 18 described in Example 2. The incubation protocol was virus plus serum incubated at 37° C. for one hour.

Table 3D (HIVNT6P1.XLS) depicts the results obtained with sera derived from monkeys immunized with peptides gp120-31–gp120-40. The cells used were H9 NY and the virus used was HTLV-IIIB, Batch 18 described in Example 2. The incubation protocol was (virus plus serum) incubation at 37° C. for one hour.

Table 4 (HIVTAB4.XLS) shows the results of the first retest of putative neutralizing antibodies as determined by the first test (Tables 3A–D). In each test, the virus used was HTLV-IIIB, Batch 18 and the cells used were H9 NY. The First Retest results in rows 1–19 are the results of neutralization test number 5. The incubation protocol was incubation at 37° C. for one hour. The First Retest results in rows 20–32 are the results of neutralization test number 7. The incubation protocol was incubation of at 37° C. for one hour.

Table 5 (HIVTAB5.XLS) shows second, third and fourth retest results of the positive peptides. In each test, the virus used was HTLV-IIIB, Batch 18 and the cells used were H9 NY. The Second Retest results in rows 1–4 are the results of neutralization test number 7. The incubation protocol was incubation at 37° C. for one hour. The Second Retest results in rows 5–13 are the results of neutralization test number 12. The Third Retest results shown in rows 14–16 are the results of neutralization test number 12. The incubation protocol was incubation of at 37° C. for one hour. The Fourth Retest results shown in rows 17–39 are the results of neutralization test number 16. The incubation protocol was incubation of at 4° C. for 16 hours. The Second Retest results in rows 40–53 are the result of neutralization test 19. The incubation protocol was cells plus virus at 4° C. for 16 hours.

Table 6 (HIVKOMBP.XLS) shows the neutralization assay results with combined hyperimmune sera. Note that the incubation of virus and cells was at 4° C. for 16 hours.

The results depicted in Tables 3(A–D)–6 indicate that the peptides of the present invention elicit the production of HIV neutralizing antibodies in primate subjects. The use of the peptides in vaccination of human subjects is therefore applicable to prevent infection by HIV or to induce heightened immune response in subjects already infected by HIV.

TABLE 3A

ASSAYS OF ANTISERA TO PEPTIDES gp120-1–gp120-10

| PEPTIDE | Serum Dilution | P-24 ANTIGEN (Supernatant DIL) | | | RELATIVE AMOUNT OF AG POS CELLS |
|---|---|---|---|---|---|
| | | 1/10 | 1/100 | 1/1000 | |
| 1. Pos control | | >2.0 | 1.176 | 0.158 | +++ |
| 2. Pos control | | >2.0 | 1.194 | 0.177 | +++ |
| 3. Pos control | | >2.0 | >2.0 | 0.464 | +++ |
| 4. Neg control | | 0.056 | – | – | – |
| 5. guinea pig | 1/10 | 0.178 | 0.066 | 0.063 | – |
| 6. Pos control | 1/40 | 0.71 | 0.118 | 0.06 | ++ |
| 7. Antiserum | 1/160 | >2.0 | 0.742 | 0.11 | ++ |
| 8. | 1/320 | >2.0 | 0.484 | 0.093 | +++ |
| 9. preimmune | | ND | ND | ND | ND |
| 10. gp120-1 | 1/5 | 0.715 | 0.108 | 0.054 | ++ |
| 11. | 1/20 | >2.0 | 0.36 | 0.073 | ++ |
| 12. | 1/80 | >2.0 | 0.57 | 0.093 | ++ |
| 13. preimmune | | >2.0 | 0.437 | 0.081 | ++ |

TABLE 3A-continued

ASSAYS OF ANTISERA TO PEPTIDES gp120-1–gp120-10

| PEPTIDE | Serum Dilution | P-24 ANTIGEN (Supernatant DIL) | | | RELATIVE AMOUNT OF AG POS CELLS |
|---|---|---|---|---|---|
| | | 1/10 | 1/100 | 1/1000 | |
| 14. gp120-2 | 1/5 | >2.0 | 0.86 | 0.138 | ++ |
| 15. | 1/20 | >2.0 | 0.486 | 0.093 | +++ |
| 16. | 1/80 | >2.0 | 0.257 | 0.083 | +++ |
| 17. preimmune | | >2.0 | 0.466 | 0.09 | ++ |
| 18. gp120-3 | 1/5 | >2.0 | 0.367 | 0.079 | ++ |
| 19. | 1/20 | >2.0 | 0.512 | 0.094 | ++ |
| 20. | 1/80 | >2.0 | 0.724 | 0.113 | ++ |
| 21. preimmune | | >2.0 | 0.536 | 0.094 | ++ |
| 22. gp120-4 | 1/5 | >2.0 | 0.638 | 0.092 | ++ |
| 23. | 1/20 | >2.0 | 0.448 | 0.082 | ++ |
| 24. | 1/80 | >2.0 | 0.592 | 0.097 | ++ |
| 25. preimmune | | >2.0 | 0.43 | 0.082 | ++ |
| 26. gp120-5 | 1/5 | >2.0 | 0.638 | 0.098 | ++ |
| 27. | 1/20 | >2.0 | 0.737 | 0.11 | ++ |
| 28. | 1/80 | >2.0 | 0.786 | 0.119 | +++ |
| 29. preimmune | | >2.0 | 0.822 | 0.125 | ++ |
| 30. gp120-6 | 1/5 | >2.0 | 0.716 | 0.131 | +++ |
| 31. | 1/20 | >2.0 | 0.977 | 0.119 | ++ |
| 32. | 1/80 | >2.0 | 0.861 | 0.124 | ++ |
| 33. preimmune | | >2.0 | 0.719 | 0.116 | ++ |
| 34. gp120-7 | 1/5 | >2.0 | 0.587 | 0.106 | ++ |
| 35. | 1/20 | >2.0 | 0.45 | 0.092 | ++ |
| 36. | 1/80 | >2.0 | 0.756 | 0.117 | ++ |
| 37. preimmune | | >2.0 | 0.507 | 0.096 | +++ |
| 38. gp120-8 | 1/5 | >2.0 | 0.555 | 0.098 | ++ |
| 39. | 1/20 | >2.0 | 0.59 | 0.103 | ++ |
| 40. | 1/80 | >2.0 | 0.308 | 0.081 | ++ |
| 41. preimmune | | >2.0 | 0.322 | 0.076 | +++ |
| 42. gp120-9 | 1/5 | >2.0 | 0.358 | 0.09 | ++ |
| 43. | 1/20 | >2.0 | 0.403 | 0.082 | +++ |
| 44. | 1/80 | >2.0 | 0.612 | 0.102 | +++ |
| 45. preimmune | | >2.0 | 0.747 | 0.127 | ++ |
| 46. gp120-10 | 1/5 | >2.0 | 0.3 | 0.074 | ++ |
| 47. | 1/20 | >2.0 | 0.426 | 0.092 | ++ |
| 48. | 1/80 | >2.0 | 0.442 | 0.083 | ++ |

TABLE 3B

ASSAYS OF ANTISERA TO PEPTIDES gp120-11–gp120-20

| PEPTIDE | Serum Dilution | P-24 ANTIGEN (Supernatant DIL) | | | RELATIVE AMOUNT OF AG POS CELLS |
|---|---|---|---|---|---|
| | | 1/10 | 1/100 | 1/1000 | |
| 1. preimmune | 1/5 | >2.0 | 0.882 | 0.149 | ++ |
| 2. gp120-11 | 1/5 | >2.0 | 0.73 | 0.135 | ++ |
| 3. | 1/20 | >2.0 | 1.73 | 0.299 | ++ |
| 4. | 1/80 | >2.0 | 0.700 | 0.148 | ++ |
| 5. preimmune | 1/5 | >2.0 | 1.07 | 0.151 | ++ |
| 6. gp120-12 | 1/5 | 0.157 | 0.07 | 0.076 | + |
| 7. | 1/20 | >2.0 | 1.45 | 0.22 | ++ |
| 8. | 1/80 | >2.0 | 1.37 | 0.221 | ++ |
| 9. preimmune | 1/5 | >2.0 | 0.58 | 0.107 | ++ |
| 10. gp120-13 | 1/5 | >2.0 | 1.16 | 0.194 | ++ |
| 11. | 1/20 | 1.816 | 0.37 | 0.095 | ++ |
| 12. | 1/80 | >2.0 | 1.16 | 0.187 | ++ |
| 13. preimmune | 1/5 | >2.0 | >2.0 | 0.281 | ++ |
| 14. gp120-14 | 1/5 | >2.0 | 0.81 | 0.142 | ++ |
| 15. | 1/20 | >2.0 | 1.39 | 0.219 | ++ |
| 16. | 1/80 | >2.0 | 0.83 | 0.156 | ++ |
| 17. preimmune | 1/5 | >2.0 | 1.13 | 0.192 | ++ |
| 18. gp120-15 | 1/5 | >2.0 | 1.43 | 0.243 | ++ |
| 19. | 1/20 | 0.069 | 0.05 | 0.05 | – |
| 20. | 1/80 | >2.0 | 0.57 | 0.104 | ++ |
| 21. preimmune | 1/5 | >2.0 | 1.78 | 0.303 | ++ |
| 22. gp120-16 | 1/5 | 0.26 | 0.07 | 0.056 | + |

TABLE 3B-continued

ASSAYS OF ANTISERA TO PEPTIDES gp120-11–gp120-20

| PEPTIDE | Serum Dilution | P-24 ANTIGEN (Supernatant DIL) | | | RELATIVE AMOUNT OF AG POS CELLS |
|---|---|---|---|---|---|
| | | 1/10 | 1/100 | 1/1000 | |
| 23. | 1/20 | 0.067 | 0.06 | 0.054 | – |
| 24. | 1/80 | >2.0 | 0.74 | 0.132 | ++ |
| 25. preimmune | 1/5 | >2.0 | 1.13 | 0.171 | ++ |
| 26. gp120-17 | 1/5 | >2.0 | 0.76 | 0.161 | ++ |
| 27. | 1/20 | >2.0 | 1.56 | 0.285 | ++ |
| 28. | 1/80 | >2.0 | 0.7 | 0.129 | ++ |
| 29. preimmune | 1/5 | >2.0 | 1.41 | 0.177 | ++ |
| 30. gp120-18 | 1/5 | >2.0 | >2.0 | 0.339 | ++ |
| 31. | 1/20 | >2.0 | 1.36 | 0.218 | ++ |
| 32. | 1/80 | >2.0 | 1.26 | 0.199 | ++ |
| 33. preimmune | 1/5 | >2.0 | 0.39 | 0.097 | ++ |
| 34. gp120-19 | 1/5 | 0.476 | 0.1 | 0.061 | + |
| 35. | 1/20 | 1.048 | 0.18 | 0.068 | + |
| 36. | 1/80 | >2.0 | 1.62 | 0.303 | ++ |
| 37. preimmune | 1/5 | >2.0 | 1.11 | 0.189 | ++ |
| 38. gp120-20 | 1/5 | >2.0 | 1.19 | 0.182 | ++ |
| 39. | 1/20 | >2.0 | 1.47 | 0.054 | ++ |
| 40. | 1/80 | >2.0 | 1.42 | 0.264 | ++ |

TABLE 3C

ASSAY OF ANTISERA TO PEPTIDES 21–30

| PEPTIDE | Serum Dilution | P-24 ANTIGEN (Supernatant DIL) | | | RELATIVE AMOUNT OF AG FOR CELLS | NO. OF SYNCYTIA/WELL | |
|---|---|---|---|---|---|---|---|
| | | 1/10 | 1/100 | 1/1000 | | Day 5 | Day 7 |
| 49. pos control | | >2.0 | 0.65 | 0.09 | ++ | 12 | 72 |
| 50. pos control | | 1.85 | 0.24 | 0.061 | ++ | 6 | 27 |
| 51. neg control | | 0.4 | | | | 0 | 0 |
| 52. guinea pig | 1/10 | 0.5 | 0.04 | 0.047 | – | 0 | 0 |
| 53. pos control | 1/40 | 0.05 | 0.04 | 0.04 | – | 1 | 0 |
| 54. antiserum | 1/160 | 0.04 | 0.05 | 0.043 | + | 1 | 3 |
| 55. | 1/640 | 1.07 | 0.14 | 0.056 | + | 2 | 19 |
| 56. preimmune | 1/5 | >2.0 | 1.57 | 0.275 | | 12 | 85 |
| 57. gp120-21 | 1/5 | >2.0 | 0.4 | 0.075 | ++ | 3 | 28 |
| 58. | 1/20 | 1 | 0.17 | 0.059 | | 5 | 21 |
| 59. | 1/80 | >2.0 | 0.48 | 0.089 | | 7 | 72 |
| 60. preimmune | 1/5 | >2.0 | 1.1 | 0.182 | | 3 | ND |
| 61. gp120-22 | 1/5 | >2.0 | 1.48 | 0.221 | ++ | 2 | 75 |
| 62. | 1/20 | >2.0 | 1.07 | 0.16 | | 0 | 80 |
| 63. | 1/80 | >2.0 | 0.63 | 0.087 | | 5 | 90 |
| 64. preimmune | 1/5 | >2.0 | 0.4 | 0.083 | | 4 | 52 |
| 65. gp120-23 | 1/5 | 1.97 | 0.26 | 0.067 | ND | 0 | 20 |
| 66. | 1/20 | >2.0 | 1.63 | 0.236 | | 5 | 98 |
| 67. | 1/80 | >2.0 | 0.35 | 0.084 | | 5 | >150 |
| 68. preimmune | 1/5 | >2.0 | >2.0 | 0.355 | | 2 | 49 |
| 69. gp120-24 | 1/5 | 1.95 | 0.29 | 0.067 | + | 0 | 3 |
| 70. | 1/20 | >2.0 | 0.37 | 0.081 | | 5 | 34 |
| 71. | 1/80 | 1.87 | 0.24 | 0.069 | | 3 | 48 |
| 72. preimmune | 1/5 | >2.0 | 0.83 | 0.145 | | 0 | 91 |
| 73. gp120-25 | 1/5 | >2.0 | 0.73 | 0.11 | ++ | 1 | 25 |
| 74. | 1/20 | 1.63 | 0.23 | 0.062 | | 0 | 15 |
| 75. | 1/80 | 1.88 | 0.22 | 0.064 | | 0 | 38 |
| 76. preimmune | 1/5 | >2.0 | 0.48 | 0.089 | | 0 | 79 |
| 77. gp120-26 | 1/5 | >2.0 | 0.62 | 0.101 | ++ | 3 | 91 |
| 78. | 1/20 | >2.0 | 0.34 | 0.063 | | 3 | 35 |
| 79. gp120-26 | 1/80 | 1.27 | 0.19 | 0.061 | | 0 | 21 |
| 80. preimmune | 1/5 | >2.0 | 0.66 | 0.11 | | 2 | 52 |
| 81. gp120-27 | 1/5 | >2.0 | 0.58 | 0.098 | ++ | 1 | 26 |
| 82. | 1/20 | >2.0 | 0.65 | 0.099 | | 6 | 49 |
| 83. | 1/80 | >2.0 | 0.3 | 0.062 | | 2 | 35 |
| 84. preimmune | 1/5 | >2.0 | >2.0 | 0.317 | | 7 | 31 |
| 85. gp120-28 | 1/5 | >2.0 | 0.39 | 0.078 | ++ | 2 | 22 |
| 86. | 1/20 | >2.0 | 0.68 | 0.105 | | 5 | 70 |

TABLE 3C-continued

ASSAY OF ANTISERA TO PEPTIDES 21–30

| PEPTIDE | Serum Dilution | P-24 ANTIGEN (Supernatant DIL) | | | RELATIVE AMOUNT OF AG FOR CELLS | NO. OF SYNCYTIA/WELL | |
|---|---|---|---|---|---|---|---|
| | | 1/10 | 1/100 | 1/1000 | | Day 5 | Day 7 |
| 87. | 1/80 | 0.99 | 0.15 | 0.05 | | 3 | >150 |
| 88. preimmune | 1/5 | >2.0 | 1.29 | 0.187 | | 5 | 97 |
| 89. gp120-29 | 1/5 | >2.0 | 0.55 | 0.096 | ++ | 3 | 112 |
| 90. | 1/20 | >2.0 | 0.85 | 0.135 | | 3 | >150 |
| 91. | 1/80 | >2.0 | 0.72 | 0.113 | | 0 | 29 |
| 92. preimmune | 1/5 | >2.0 | >2.0 | 0.326 | | 10 | 130 |
| 93. gp120-30 | 1/5 | >2.0 | 0.27 | 0.073 | + | 3 | 38 |
| 94. | 1/20 | >2.0 | 1.71 | 0.24 | | 9 | 52 |
| 95. | 1/80 | >2.0 | 0.44 | 0.083 | | 6 | ND |

TABLE 3D

ASSAYS OF ANTISERA TO PEPTIDES 31–40

| PEPTIDE | Serum Dilution | P-24 ANTIGEN (Supernatant DIL) | | | RELATIVE AMOUNT OF AG FOR CELLS | NO. OF SYNCYTIA/WELL Day 5 |
|---|---|---|---|---|---|---|
| | | 1/10 | 1/100 | 1/1000 | | |
| 96. pos control | | 0.976 | 0.258 | 0.123 | | 6 |
| 97. pos control | | 1.836 | 0.656 | 0.185 | | 11 |
| 98. neg control | | | | | | |
| 99. guinea pig | 1/10 | 0.103 | 0.088 | 0.09 | | 0 |
| 100. pos control | 1/40 | 0.104 | 0.087 | 0.093 | | 0 |
| 101. antiserum | 1/160 | 0.749 | 0.29 | 0.1 | | 4 |
| 102. | 1/640 | 1.066 | 0.238 | 0.237 | | 7 |
| 103. preimmune | 1/5 | 0.824 | | | | |
| 104. gp120-31 | 1/5 | 1.769 | 0.675 | 0.186 | | 47 |
| 105. | 1/20 | 1.124 | 0.302 | 0.111 | | 22 |
| 106. | 1/80 | 0.978 | 0.258 | ND | | 24 |
| 107. preimmune | 1/5 | 0.883 | | | | |
| 108. gp120-32 | 1/5 | 1.163 | 0.258 | ND | | 7 |
| 109. | 1/20 | 1.482 | 0.311 | ND | | 8 |
| 110. | 1/80 | 0.996 | 0.263 | ND | | 0 |
| 111. preimmune | 1/5 | 1.76 | | | | |
| 112. gp120-33 | 1/5 | 0.84 | 0.239 | 0.156 | | 20 |
| 113. | 1/20 | 1.282 | 0.333 | 0.144 | | 16 |
| 132. gp120-38 | 1/5 | 1.386 | 0.59 | 0.114 | | 11 |
| 133. | 1/20 | 0.576 | 0.214 | 0.106 | | 17 |
| 134. | 1/80 | 1.23 | 0.329 | ND | | |
| 135. preimmune | 1/5 | 1.854 | | | | |
| 136. gp120-39 | 1/5 | 1.376 | 0.495 | 0.182 | | 28 |
| 137. | 1/20 | 0.711 | 0.296 | 0.118 | | 17 |
| 138. | 1/80 | 0.929 | 0.237 | ND | | |
| 139. preimmune | 1/5 | ND | | | | |
| 140. gp120-40 | 1/5 | 0.862 | 0.255 | 0.132 | | 13 |
| 141. | 1/20 | 0.989 | 0.273 | 0.143 | | 10 |
| 142. | 1/80 | 0.477 | 0.164 | ND | | |

TABLE 4

RETESTING OF HYPERIMMUNE SERA WITH THE CAPACITY TO NEUTRALIZE HIV

| PEPTIDE | Serum Dilution | P-24 ANTIGEN (Supernatant DIL) | | | RELATIVE AMOUNT OF AG FOR CELLS | NO. OF SYNCYTIA/WELL | |
|---|---|---|---|---|---|---|---|
| | | 1/10 | 1/100 | 1/1000 | | Day 5 | Day 7 |
| First Retest | | | | | | | |
| 1. pos control | | >2.0 | 0.646 | 0.09 | ++ | 12 | 72 |
| 2. pos control | | 1.853 | 0.244 | 0.061 | ++ | 6 | 27 |
| 3. neg control | | 0.039 | | | | 0 | 0 |
| 4. guinea pig | 1/10 | 0.051 | 0.04 | 0.047 | − | 0 | 0 |
| 5. pos control | 1/40 | 0.052 | 0.042 | 0.04 | − | 1 | 0 |
| 6. antiserum | 1/160 | 0.042 | 0.046 | 0.043 | + | 1 | 3 |
| 7. | 1/640 | 1.067 | 0.144 | 0.056 | + | 2 | 19 |

TABLE 4-continued

RETESTING OF HYPERIMMUNE SERA WITH THE CAPACITY TO NEUTRALIZE HIV

| | | | | | | | |
|---|---|---|---|---|---|---|---|
| 8. preimmune | 1/5 | 2 | 1.326 | 0.172 | | 10 | 112 |
| 9. gp120-12 | 1/5 | 1.083 | 0.153 | 0.06 | + | 1 | 24 |
| 10. | 1/20 | 2 | 1.487 | 0.171 | | 7 | 175 |
| 11. | 1/80 | 2 | 0.463 | 0.07 | | 6 | ND |
| 12. preimmune | 1/5 | 2 | 1.991 | 0.237 | | 2 | 64 |
| 13. gp120-16 | 1/5 | 2 | 0.355 | 0.07 | + | 0 | 13 |
| 14. | 1/20 | 0.741 | 0.103 | 0.048 | | 0 | 11 |
| 15. | 1/80 | 2 | 0.32 | 0.08 | | 0 | 35 |
| 16. preimmune | 1/5 | >2.0 | 0.547 | 0.082 | | 3 | 42 |
| 17. gp120-19 | 1/5 | 0.141 | 0.062 | 0.053 | + | 0 | 6 |
| 18. | 1/20 | 1.134 | 0.164 | 0.054 | | 0 | 26 |
| 19. | 1/80 | >2.0 | 0.455 | 0.081 | | 1 | 45 |

| PEPTIDE | Serum Dilution | P-24 ANTIGEN (Supernatant DIL) | | | RELATIVE AMOUNT OF AG FOR CELLS | NO. OF SYNCYTIA/WELL | |
|---|---|---|---|---|---|---|---|
| | | 1/5 | 1/50 | 1/500 | | Day 7 | Day 10 |
| First Retest | | | | | | | |
| 20. pos control | | 1.175 | 0.426 | 0.201 | | 9 | 46 |
| 21. pos control | | 1.529 | 0.401 | 0.161 | | 32 | 167 |
| 22. neg control | | | | | | | |
| 23. guinea pig | 1/10 | 0.139 | 0.165 | 0.145 | − | 0 | 0 |
| 24. pos control | 1/40 | 0.211 | 0.159 | 0.168 | − | 1 | 0 |
| 25. antiserum | 1/160 | 0.961 | 0.299 | 0.163 | ++ | 9 | 26 |
| 26. | 1/640 | 0.989 | 0.26 | 0.159 | ++ | 5 | 20 |
| 27. gp120-24 | 1/5 | 1.067 | 0.245 | 0.166 | ++ | 4 | 34 |
| 28. | 1/20 | 0.795 | 0.204 | 0.167 | ++ | 5 | 41 |
| 29. | 1/80 | 0.433 | 0.167 | | − | 15 | 80 |
| 30. gp120-25 | 1/5 | 1.237 | 0.282 | 0.155 | ++ | 19 | 144 |
| 31. | 1/20 | 1.312 | 0.373 | 0.187 | ++ | 42 | 116 |
| 32. | 1/80 | ND | ND | ND | − | ND | ND |

TABLE 5

RETESTING OF HYPERIMMUNE SERA WITH CAPACITY TO NEUTRALIZE HTLV-III

| PEPTIDE | Serum Dilution | P-24 ANTIGEN (Supernatant DIL) | | | *RELATIVE AMOUNT OF AG FOR CELLS | NO. OF SYNCYTIA/WELL | |
|---|---|---|---|---|---|---|---|
| Second Retest | | 1/5 | 1/50 | 1/500 | | Day 5 | Day 7 |
| 1. gp120-16 | 1/5 | ND | ND | ND | | ND | ND |
| 2. | 1/5 | 1.924 | 1.062 | 0.282 | ++ | | |
| 3. | 1/20 | 0.365 | 0.172 | 0.145 | − | 2 | 5 |
| 4. | 1/80 | 0.163 | 0.133 | | − | 0 | 0 |
| Second Retest | | 1/10 | 1/100 | 1/1,000 | | | |
| 5. pos control | | >2.0 | >2.0 | 1.026 | +++ | 320 | |
| 6. pos control | | >2.0 | >2.0 | 0.639 | +++ | 220 | |
| 7. pos control | | >2.0 | >2.0 | 0.866 | +++ | 290 | |
| 8. pos control | | >2.0 | >2.0 | 0.881 | | | |
| 9. neg control | | 0.223 | | | − | | |
| 10. neg control | | 0.16 | | | − | | |
| 11. gp120-24 | 1/5 | >2.0 | >2.0 | 0.545 | +++ | 112 | |
| 12. | 1/20 | >2.0 | >2.0 | 0.819 | +++ | 138 | |
| 13. | 1/80 | >2.0 | >2.0 | | +++ | 230 | |
| Third Retest | | | | | | | |
| 14. gp120-16 | 1/5 | 0.122 | 0.1 | 0.115 | − | 0 | |
| | | 1/5 | 1/50 | 1/500 | | | |
| 15. | 1/20 | >2.0 | 1.14 | 0.352 | ++ | 0 | |
| 16. | 1/80 | >2.0 | >2.0 | | +++ | 210 | |
| Fourth Retest | | | | | | | |
| 17. pos control | | 1.425 | 0.732 | 0.154 | ++ | 16 | |
| 18. pos control | | 1.346 | 0.672 | 0.152 | +++ | 16 | |
| 19. pos control | | 1.431 | 0.545 | 0.182 | +++ | 17 | |
| 20. pos control | | 1.414 | 0.931 | 0.251 | | | |
| 21. neg control | | 0.067 | | | − | | |

TABLE 5-continued

RETESTING OF HYPERIMMUNE SERA WITH CAPACITY TO NEUTRALIZE HTLV-III

| PEPTIDE | Serum Dilution | P-24 ANTIGEN (Supernatant DIL) | | | *RELATIVE AMOUNT OF AG FOR CELLS | NO. OF SYNCYTIA/WELL Day 5 | NO. OF SYNCYTIA/WELL Day 7 |
|---|---|---|---|---|---|---|---|
| 22. neg control | | 0.045 | | | – | | |
| 23. neg control | | 0.042 | | | – | | |
| 24. guinea pig | 1/10 | 0.044 | 0.037 | 0.029 | | 0 | |
| 25. pos control | 1/40 | 0.063 | 0.039 | 0.029 | | 0 | |
| 26. antiserum | 1/160 | 0.036 | 0.035 | 0.055 | | 0 | |
| 27. | 1/640 | 0.556 | 0.072 | 0.034 | | 1 | |
| 28. gp120-12 | 1/8 | 0.072 | 0.043 | 0.046 | | 0 | |
| 29. | 1/32 | 0.169 | 0.054 | 0.047 | | 0 | |
| 30. | 1/128 | >2.0 | 1.124 | 0.241 | | 19 | |
| 31. gp120-16 | 1/8 | 0.043 | 0.045 | 0.049 | | 0 | |
| 32. | 1/32 | 0.052 | 0.043 | 0.048 | | 0 | |
| 33. | 1/128 | 1.54 | 0.903 | 0.014 | | 4 | |
| 34. gp120-19 | 1/8 | 0.105 | 0.043 | 0.042 | | 0 | |
| 35. | 1/32 | 0.358 | 0.08 | 0.045 | | 5 | |
| 36. | 1/128 | >2.0 | 0.944 | 0.205 | | 25 | |
| 37. gp120-24 | 1/8 | >2.0 | 0.885 | 0.155 | | 2 | |
| 38. | 1/32 | >2.0 | 1.174 | 0.293 | | 15 | |
| 39. | 1/128 | 1.158 | 0.858 | 0.213 | | 11 | |
| Second Retest | | | | | | | |
| 40. pos control | | 0.916 | 0.166 | 0.099 | | | 74 |
| 41. pos control | | 1.607 | 0.469 | 0.151 | | | 130 |
| 42. pos control | | >2.0 | 0.943 | 0.203 | | | 123 |
| 43. pos control | | 1.445 | 0.319 | 0.082 | | | 195 |
| 44. neg control | | 0.145 | | | | | |
| 45. neg control | | 0.326 | | | | | |
| 46. guinea pig | 1/10 | 0.09 | 0.111 | 0.075 | | | 0 |
| 47. pos control | 1/140 | 0.096 | 0.082 | 0.078 | | | 0 |
| 48. antiserum | 1/160 | 0.094 | 0.109 | 0.091 | | | 0 |
| 49. | 1/640 | 0.996 | 0.212 | 0.104 | | | 35 |
| 50. preimmune | 1/5 | >2.0 | 0.444 | 0.162 | | | 95 |
| 51. gp120-15 | 1/5 | 0.155 | 0.094 | 0.111 | | | ND |
| 52. | 1/20 | 0.152 | 0.109 | 0.158 | | | 4 |
| 53. | 1/80 | 0.176 | 0.13 | 0.207 | | | 0 |

TABLE 6

COMBINED NEUTRALIZATION EFFECTS OF SERA FROM MONKEYS

| PEPTIDE | Serum Dilution | P-21 ANTIGEN (Supernatant DIL) 1/5 | 1/50 | 1/500 | NT TITRE OF SERUM | RELATIVE AMOUNT OF AG POS CELLS | NO. OF SYNCYTIA/WELL Day 6 |
|---|---|---|---|---|---|---|---|
| 1. Pos control | | 1.4 | 0.7 | 0.154 | | ++ | 16 |
| 2. Pos control | | 1.3 | 0.7 | 0.152 | | +++ | 16 |
| 3. Pos control | | 1.4 | 0.8 | 0.182 | | | 17 |
| 4. Pos control | | 1.4 | 0.9 | 0.251 | | | |
| 5. neg control | | 0.1 | | | | – | |
| 6. neg control | | 0 | | | | – | |
| 7. neg control | | 0 | | | | – | |
| 8. guinea pig | 1/10 | 0 | 0 | 0.029 | | | 0 |
| 9. pos control | 1/40 | 0.1 | 0 | 0.029 | | | 0 |
| 10. antiserum | 1/160 | 0 | 0 | 0.055 | 160 | | 0 |
| 11. | 1/640 | 0.6 | 0.1 | 0.034 | | | 1 |
| 12. Group I | 1/8 | 0 | 0 | 0.038 | | | 1 |
| 13. gp120.mix | 1/32 | 0 | 0 | 0.041 | | | 0 |
| 14. 12 + 16 + 19 + 24 | 1/128 | 0.2 | 0.1 | 0.043 | >128 | – | 0 |
| 15. Group II | 1/8 | 0.1 | 0 | 0.046 | | | 0 |
| 16. gp120.mix | 1/32 | 0.1 | 0.1 | 0.046 | | – | 0 |
| 17. 16 + 19 | 1/128 | 0.1 | 0.2 | 0.043 | >128 | – | 0 |
| 18. Group III | 1/8 | 0 | 0 | 0.051 | | | 0 |
| 19. gp120.mix | 1/32 | 0.1 | 0.1 | 0.043 | | – | 0 |
| 20. 16 + 24 | 1/128 | 1 | 0.3 | 0.065 | 128 | ++ | 1 |
| 21. Group IV | 1/8 | 0.2 | 0 | 0.044 | | | 2 |
| 22. gp120.mix | 1/32 | 0.1 | 0 | 0.045 | | – | 1 |
| 23. 16 + 12 | 1/128 | 0.2 | 0.1 | 0.048 | >128 | – | 0 |
| 24. gp120-12 | 1/8 | 0.1 | 0 | 0.046 | | – | 0 |
| 25. | 1/32 | 0.2 | 0.1 | 0.047 | 32 | + | 0 |

TABLE 6-continued

COMBINED NEUTRALIZATION EFFECTS OF SERA FROM MONKEYS

| PEPTIDE | Serum Dilution | P-21 ANTIGEN (Supernatant DIL) | | | NT TITRE OF SERUM | RELATIVE AMOUNT OF AG POS CELLS | NO. OF SYNCYTIA/WELL Day 6 |
|---|---|---|---|---|---|---|---|
| | | 1/5 | 1/50 | 1/500 | | | |
| 26. | 1/128 | 1.3 | 1.1 | 0.241 | | | 19 |
| 27. gp120-16 | 1/8 | 0 | 0 | 0.049 | | | 0 |
| 28. | 1/32 | 0.1 | 0 | 0.048 | 32 | – | 0 |
| 29. | 1/128 | 1.5 | 0.9 | 0.138 | | – | 4 |
| 30. gp120-19 | 1/8 | 0.1 | 0 | 0.042 | | – | 0 |
| 31. | 1/32 | 0.4 | 0.1 | 0.045 | 32 | – | 5 |
| 32. | 1/128 | >3 | 0.9 | 0.205 | | ++ | 25 |
| 33. gp120-24 | 1/8 | 3 | 0.9 | 0.155 | neg | | 2 |
| 34. | 1/32 | >3 | 1.2 | 0.293 | | | 15 |
| 35. | 1/128 | 1.2 | 0.9 | 0.213 | | | 11 |

EXAMPLE 6

The ADCC Assay

The method used for determination of HIV specific ADCC has been described by Ljunggren et al. J. Immunol. Meth. 1987, 104:7; J. Immunol., 139:2263 (1987). Briefly, the cell line U937 clone 2, continuously infected with HIV-1$_{HTLVIIIB}$ was used as target cells. Peripheral blood mononuclear cells (PBMC) obtained from HIV antibody negative blood donors were used as effector cells. The PBMC were collected by density centrifugation on LYMPHOPREP lymphocyte separation medium (Nykomed Pharma AS, Oslo, Norway) and adherent cells were removed by the scrubbed nylon wool technique, Merril et al. Eur. J. Immunol., 11:536 (1981). $^{51}$Cr-labeled target cells, $1\times10^4$, and lymphocytes as effector cells, $2\times10^5$, were mixed with serum dilutions, six dilution steps in three-fold serial dilutions starting at 1:30. Supernatants were harvested after three hours and released radioactivity was calculated. The spontaneous release never exceeded 10%.

HIV specific ADCC was determined as follows: specific $^{51}$Cr-release with HIV positive sera minus specific $^{51}$Cr-release with HIV negative sera. Sera with a Specific ADCC Index (SAI) value >0.5 at 1:30 were considered to be positive for HIV-specific ADCC, Ljunggren et al. J. Immunol. 1987, 139:2263. This value represents more than 3 SD above the specific $^{51}$Cr-release obtained by HIV-antibody negative sera. HIV antibody positive sera with known ADCC titer were included in each test. The reciprocal of the last dilution step with an SAI-value >0.5 was taken as the ADCC titer. No ADCC activity could be detected in any sera against uninfected target cells or in any HIV antibody negative control sera.

The hyperimmune sera determined according to Example 5 above were tested in an ADCC assay as described above. The results for ADCC positive sera only are presented in Table 7 below. All other sera in the group were ADCC negative. All preimmune sera in monkeys 1–40 were negative against infected target cells except serum no. 36 that had a titer of 1:30. All preimmune and hyperimmune sera were ADCC negative against uninfected target cells.

TABLE 7

ADCC positive anti-sera raised in monkeys against peptides representing HIV-1$_{HTLVIIIB}$ gp120

| anti-sera against | amino acid # | ADCC titer |
|---|---|---|
| gp120-1 | 1–28 | 7290* |
| gp120-5 | 65–89 | 2430 |
| gp120-6 | 75–100 | 2430 |
| gp120-7 | 90–116 | 810 |
| gp120-8 | 101–126 | 90 |
| gp120-12 | 152–176 | 2430 |
| gp120-14 | 177–205 | 90 |
| gp120-16/B | 213–224 | 2430 |
| gp120-19 | 248–269 | 7290 |
| gp120-20 | 258–282 | 2430 |
| gp120-21 | 270–295 | 90 |
| gp120-23 | 296–320 | 90 |
| gp120-24 | 307–330 | 30 |
| gp120-36 | 445–466 | 2430 |

*This serum was negative in one out of three experiments; in two experiments the ADCC titer was 7290.

The results depicted in Table 7 indicate that the peptides of the present invention include linear ADCC epitopes specific for HIV-1$_{HTLVIIIB}$ gp120. Thus, the peptides of the present invention can be used to induce antibody-dependent cellular cytotoxicity to aid in the prevention of infection by HIV or to induce a heightened immune response in subjects already infected with HIV.

To determine the precise amino acids necessary for the active epitope for each of the novel peptides of the present invention, deletion analysis can be performed as described in the following example.

EXAMPLE 7

Deletion Analysis of the Peptides

The peptides of the present invention may be used in exactly the form described herein, or may be used in supplemented or truncated active form. In order to determine whether removal or addition of amino acids to the sequence affects the beneficial properties of that sequence as described above, routine experimentation may be conducted to identify that portion of the sequence containing the active epitope. For example, deletion analysis is performed on gp120-1 by synthesizing peptides lacking one, two, three, or more amino acids from the carboxy terminus, from the amino terminus, or both, and testing those peptides systematically in accordance with Examples 4–6. If the resulting truncated peptide is immunologically equivalent to the untruncated form in generating protective or neutralizing antibodies, then one can conclude that the epitope responsible for the properties in question is found within the truncated sequence. Similarly, the sequences can be tested after addition of one, two, three, or more amino acids (selected from any desired amino acid) to either end of the peptide. If the resulting peptide substantially retains the properties identified in Examples 4–6 for the unmodified peptide, the modified peptide is considered immunologically equivalent for purposes of the present invention.

In addition to synthesizing the peptides to be tested de novo, amino acids can be chemically removed from the peptides of any of the SEQ ID NOs disclosed herein. For example, amino acids can be removed using the method disclosed in Morrison and Boyd, Organic Chemistry, 3d edition, pp. 1145–1146 (1976), the disclosure of which is hereby incorporated by reference. Briefly, phenyl isothiocyanate is used to form a substituted thiourea on the N-terminal residue of the peptide. Mild hydrolysis with hydrochloric acid selectively removes the N-terminal residue as the phenylthiohydantoin. The remaining peptide chain is left intact, and is assayed for immunologic activity according to the methods disclosed in Examples 4–6 described above. The procedure is then repeated, sequentially removing the N-terminal residue from the remaining peptide chain and testing the resulting peptide for its ability to induce HIV-specific ADCC, until this ability is lost. In this manner, the amino acid sequence of the active epitope is determined.

Alternatively, the C-terminal amino acid is removed selectively using the enzyme carboxypeptidase to cleave only the peptide linkages adjacent to the free alpha-carboxyl group. In addition, enzymes such as trypsin, chymotrypsin and pepsin may be used to reduce the peptides of the present invention into smaller fragments, which are then analyzed according to the methods described above in Examples 4–6.

While particular embodiments of the invention have been described in detail, it will be apparent to those skilled in the art that these embodiments are exemplary rather than limiting, and the true scope of the invention is that defined by the claims which follow.

What is claimed is:

1. A peptide consisting of an epitopic amino acid sequence from human immunodeficiency virus gp120 protein, selected from the group consisting of SEQ ID NO:1, SEQ ID NO:5, SEQ ID NO:6, SEQ ID NO:7, SEQ ID NO:8, SEQ ID NO:12, SEQ ID NO:14, SEQ ID NO:20, SEQ ID NO:21, SEQ ID NO:36 and SEQ ID NO:41 and wherein antisera raised in monkeys against said epitopic sequence has a specific antibody-dependent cellular cytotoxicity index value greater than 0.5 at a dilution greater than 1:30.

2. A composition comprising a peptide selected from the group consisting of SEQ ID NO:1, SEQ ID NO:5, SEQ ID NO:6, SEQ ID NO:7, SEQ ID NO:8, SEQ ID NO:12, SEQ ID NO:14, SEQ ID NO:20, SEQ ID NO:21, SEQ ID NO:36 and SEQ ID NO:41, in an amount effective to induce an antibody dependent cellular cytotoxic response in a primate together with a pharmaceutically acceptable carrier.

3. The composition of claim 2, further comprising an adjuvant.

4. The composition of claim 3, wherein said adjuvant is selected from the group consisting of Freund's complete adjuvant, Freund's incomplete adjuvant, muramyl dipeptide, levamisole, isoprinosine and tuftsin.

5. A composition comprising at least two peptides selected from the group consisting of SEQ ID NO:1, SEQ ID NO:5, SEQ ID NO:6, SEQ ID NO:7, SEQ ID NO:8, SEQ ID NO:12, SEQ ID NO:14, SEQ 20, SEQ ID NO:21, SEQ ID NO:36 and SEQ ID NO:41, said at least 2 peptides being present in an amount effective to induce an antibody dependent cellular cytotoxic response in a primate together with a pharmaceutically acceptable carrier.

6. The composition of claim 5, further comprising an adjuvant.

7. The composition of claim 6, wherein said adjuvant is selected from the group consisting of Freund's complete adjuvant, Freund's incomplete adjuvant, muramyl dipeptide, levamisole, isoprinosine and tuftsin.

8. A method of producing in a primate an antibody dependent cellular cytotoxic response to human immunodeficiency virus, comprising administering to said primate a composition according to claim 2.

9. A method of producing in a primate an antibody dependent cellular cytotoxic response to human immunodeficiency virus, comprising administering to said primate a composition according to claim 5.

10. The method of claim 8, wherein said administration step comprises intravenous, intramuscular, subcutaneous, or intraperitoneal injection.

11. The method of claim 9, wherein said administration step comprises intravenous, intramuscular, subcutaneous, or intraperitoneal injection.

* * * * *

SEQUENCE LISTING ( 1 ) GENERAL INFORMATION:

( i i i ) NUMBER OF SEQUENCES: 41

( 2 ) INFORMATION FOR SEQ ID NO:1:

( i ) SEQUENCE CHARACTERISTICS:
( A ) LENGTH: 28 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:1:

```
Met Arg Val Lys Glu Lys Tyr Gln His Leu Trp Arg Trp Gly Trp Arg
1               5                   10                  15

Trp Gly Thr Met Leu Leu Gly Met Leu Met Ile Cys
            20                  25
```

( 2 ) INFORMATION FOR SEQ ID NO:2:

( i ) SEQUENCE CHARACTERISTICS:
( A ) LENGTH: 24 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:2:

```
Gly Met Leu Met Ile Cys Ser Ala Thr Glu Lys Leu Trp Val Thr Val
1               5                   10                  15
```

```
        Tyr  Tyr  Gly  Val  Pro  Val  Trp  Lys
                       20
```

(2) INFORMATION FOR SEQ ID NO:3:

(i) SEQUENCE CHARACTERISTICS:
        (A) LENGTH: 24 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:3:

```
   Gly  Val  Pro  Val  Trp  Lys  Glu  Ala  Thr  Thr  Thr  Leu  Phe  Cys  Ala  Ser
   1                   5                        10                        15
   Asp  Ala  Lys  Ala  Tyr  Asp  Thr  Glu
                       20
```

(2) INFORMATION FOR SEQ ID NO:4:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:4:

```
   Cys  Ala  Ser  Asp  Ala  Lys  Ala  Tyr  Asp  Thr  Glu  Val  His  Asn  Val  Trp
   1                   5                        10                        15
   Ala  Thr  His  Ala  Cys
                       20
```

(2) INFORMATION FOR SEQ ID NO:5:

(i) SEQUENCE CHARACTERISTICS:
        (A) LENGTH: 25 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:5:

```
   Val  His  Asn  Val  Trp  Ala  Thr  His  Ala  Cys  Val  Pro  Thr  Asp  Pro  Asn
   1                   5                        10                        15
   Pro  Gln  Glu  Val  Val  Leu  Val  Asn  Val
                       20                        25
```

( 2 ) INFORMATION FOR SEQ ID NO:6:

( i ) SEQUENCE CHARACTERISTICS:
        ( A ) LENGTH: 26 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:6:

```
Val Pro Thr Asp Pro Asn Pro Gln Glu Val Val Leu Val Asn Val Thr
 1               5                  10                  15
Glu Asn Phe Asn Met Trp Lys Asn Asp Met
             20                  25
```

( 2 ) INFORMATION FOR SEQ ID NO:7:

( i ) SEQUENCE CHARACTERISTICS:
        ( A ) LENGTH: 27 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:7:

```
Thr Glu Asn Phe Asn Met Trp Lys Asn Asp Met Val Glu Gln Met His
 1               5                  10                  15
Glu Asp Ile Ile Ser Leu Trp Asp Gln Ser Leu
             20                  25
```

( 2 ) INFORMATION FOR SEQ ID NO:8:

( i ) SEQUENCE CHARACTERISTICS:
        ( A ) LENGTH: 26 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:8:

```
Val Glu Gln Met His Glu Asp Ile Ile Ser Leu Trp Asp Gln Ser Leu
 1               5                  10                  15
Lys Pro Cys Val Lys Leu Thr Pro Leu Cys
             20                  25
```

( 2 ) INFORMATION FOR SEQ ID NO:9:

( i ) SEQUENCE CHARACTERISTICS:
        ( A ) LENGTH: 25 amino acids
        ( B ) TYPE: amino acid (C) STRANDEDNESS: single
(D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:9:

Lys Pro Cys Val Lys Leu Thr Pro Leu Cys Val Ser Leu Lys Cys Thr
1               5                   10                  15
Asp Leu Lys Asn Asp Thr Asn Thr Asn
            20              25

(2) INFORMATION FOR SEQ ID NO:10:

(i) SEQUENCE CHARACTERISTICS:
    (A) LENGTH: 25 amino acids
    (B) TYPE: amino acid
    (C) STRANDEDNESS: single
    (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:10:

Val Ser Leu Lys Cys Thr Asp Leu Lys Asn Asp Thr Asn Thr Asn Ser
1               5                   10                  15
Ser Ser Gly Arg Met Ile Met Glu Lys
            20              25

(2) INFORMATION FOR SEQ ID NO:11:

(i) SEQUENCE CHARACTERISTICS:
    (A) LENGTH: 23 amino acids
    (B) TYPE: amino acid
    (C) STRANDEDNESS: single
    (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:11:

Ser Ser Ser Gly Arg Met Ile Met Glu Lys Gly Glu Ile Lys Asn Cys
1               5                   10                  15
Ser Phe Asn Ile Ser Thr Ser
            20

(2) INFORMATION FOR SEQ ID NO:12:

(i) SEQUENCE CHARACTERISTICS:
    (A) LENGTH: 25 amino acids
    (B) TYPE: amino acid
    (C) STRANDEDNESS: single
    (D) TOPOLOGY: linear (ii) MOLECULE TYPE: peptide (i i i) HYPOTHETICAL: NO (i v) ANTI-SENSE: NO (v) FRAGMENT TYPE: internal (x i) SEQUENCE DESCRIPTION: SEQ ID NO:12:

```
Gly Glu Ile Lys Asn Cys Ser Phe Asn Ile Ser Thr Ser Ile Arg Gly
1               5                   10                  15
Lys Val Gln Lys Glu Tyr Ala Phe Phe
            20                  25
```

(2) INFORMATION FOR SEQ ID NO:13:

(i) SEQUENCE CHARACTERISTICS:
        (A) LENGTH: 28 amino acids
        (B) TYPE: amino acid
        (C) STRANDEDNESS: single
        (D) TOPOLOGY: linear (i i) MOLECULE TYPE: peptide (i i i) HYPOTHETICAL: NO (i v) ANTI-SENSE: NO (v) FRAGMENT TYPE: internal (x i) SEQUENCE DESCRIPTION: SEQ ID NO:13:

```
Ile Arg Gly Lys Val Gln Lys Glu Tyr Ala Phe Phe Tyr Lys Leu Asp
1               5                   10                  15
Ile Ile Pro Ile Asp Asn Asp Thr Thr Ser Tyr Thr
            20                  25
```

(2) INFORMATION FOR SEQ ID NO:14:

(i) SEQUENCE CHARACTERISTICS:
        (A) LENGTH: 29 amino acids
        (B) TYPE: amino acid
        (C) STRANDEDNESS: single
        (D) TOPOLOGY: linear (i i) MOLECULE TYPE: peptide (i i i) HYPOTHETICAL: NO (i v) ANTI-SENSE: NO (v) FRAGMENT TYPE: internal (x i) SEQUENCE DESCRIPTION: SEQ ID NO:14:

```
Tyr Lys Leu Asp Ile Ile Pro Ile Asp Asn Asp Thr Thr Ser Tyr Thr
1               5                   10                  15
Leu Thr Ser Cys Asn Thr Ser Val Ile Thr Gln Ala Cys
            20                  25
```

(2) INFORMATION FOR SEQ ID NO:15:

(i) SEQUENCE CHARACTERISTICS:
        (A) LENGTH: 26 amino acids
        (B) TYPE: amino acid
        (C) STRANDEDNESS: single
        (D) TOPOLOGY: linear (i i) MOLECULE TYPE: peptide (i i i) HYPOTHETICAL: NO (i v) ANTI-SENSE: NO (v) FRAGMENT TYPE: internal ( x i ) SEQUENCE DESCRIPTION: SEQ ID NO:15:

Leu Thr Ser Cys Asn Thr Ser Val Ile Thr Gln Ala Cys Pro Lys Val
1               5                   10                  15

Ser Phe Glu Pro Ile Pro Ile His Tyr Cys
            20              25

( 2 ) INFORMATION FOR SEQ ID NO:16:

( i ) SEQUENCE CHARACTERISTICS:
        ( A ) LENGTH: 25 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:16:

Pro Lys Val Ser Phe Glu Pro Ile Pro Ile His Tyr Cys Ala Pro Ala
1               5                   10                  15

Gly Phe Ala Ile Leu Lys Cys Asn Asn
            20              25

( 2 ) INFORMATION FOR SEQ ID NO:17:

( i ) SEQUENCE CHARACTERISTICS:
        ( A ) LENGTH: 29 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:17:

Ala Pro Ala Gly His Ala Ile Leu Lys Cys Asn Asn Lys Thr Phe Asn
1               5                   10                  15

Gly Thr Gly Pro Cys Thr Asn Val Ser Thr Val Gln Cys
            20              25

( 2 ) INFORMATION FOR SEQ ID NO:18:

( i ) SEQUENCE CHARACTERISTICS:
        ( A ) LENGTH: 27 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:18:

Lys Thr Phe Asn Gly Thr Gly Pro Cys Thr Asn Val Ser Thr Val Gln
1               5                   10                  15

```
        Cys  Thr  His  Gly  Ile  Arg  Pro  Val  Val  Ser  Thr
                       20                       25
```

( 2 ) INFORMATION FOR SEQ ID NO:19:

( i ) SEQUENCE CHARACTERISTICS:
        ( A ) LENGTH: 22 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:19:

```
Thr  His  Gly  Ile  Arg  Pro  Val  Val  Ser  Thr  Gln  Leu  Leu  Leu  Asn  Gly
 1                  5                            10                           15

Ser  Leu  Ala  Glu  Glu  Glu
               20
```

( 2 ) INFORMATION FOR SEQ ID NO:20:

( i ) SEQUENCE CHARACTERISTICS:
        ( A ) LENGTH: 25 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:20:

```
Gln  Leu  Leu  Leu  Asn  Gly  Ser  Leu  Ala  Glu  Glu  Val  Val  Ile  Arg
 1                  5                            10                      15

Ser  Ala  Asn  Phe  Thr  Asp  Asn  Ala  Lys
               20                       25
```

( 2 ) INFORMATION FOR SEQ ID NO:21:

( i ) SEQUENCE CHARACTERISTICS:
        ( A ) LENGTH: 26 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:21:

```
Val  Val  Ile  Arg  Ser  Ala  Asn  Phe  Thr  Asp  Asn  Ala  Lys  Thr  Ile  Ile
 1                  5                            10                          15

Val  Gln  Leu  Asn  Gln  Ser  Val  Glu  Ile  Asn
               20                       25
```

( 2 ) INFORMATION FOR SEQ ID NO:22:

( i ) SEQUENCE CHARACTERISTICS:
        ( A ) LENGTH: 24 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:22:

```
Thr Ile Ile Val Gln Leu Asn Gln Ser Val Glu Ile Asn Cys Thr Arg
1               5                   10                  15
Pro Asn Asn Asn Thr Arg Lys Ser
            20
```

( 2 ) INFORMATION FOR SEQ ID NO:23:

( i ) SEQUENCE CHARACTERISTICS:
        ( A ) LENGTH: 25 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:23:

```
Cys Thr Arg Pro Asn Asn Asn Thr Arg Lys Ser Ile Arg Ile Gln Arg
1               5                   10                  15
Gly Pro Gly Arg Ala Phe Val Thr Ile
            20                  25
```

( 2 ) INFORMATION FOR SEQ ID NO:24:

( i ) SEQUENCE CHARACTERISTICS:
        ( A ) LENGTH: 24 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:24:

```
Ile Arg Ile Gln Arg Gly Pro Gly Arg Ala Phe Val Thr Ile Gly Lys
1               5                   10                  15
Ile Gly Asn Met Arg Gln Ala His
            20
```

( 2 ) INFORMATION FOR SEQ ID NO:25:

( i ) SEQUENCE CHARACTERISTICS:
        ( A ) LENGTH: 23 amino acids
        ( B ) TYPE: amino acid (C) STRANDEDNESS: single
(D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:25:

```
Gly Lys Ile Gly Asn Met Arg Gln Ala His Cys Asn Ile Ser Arg Ala
1               5                   10                  15
Lys Trp Asn Asn Thr Leu Lys
            20
```

(2) INFORMATION FOR SEQ ID NO:26:

(i) SEQUENCE CHARACTERISTICS:
(A) LENGTH: 23 amino acids
(B) TYPE: amino acid
(C) STRANDEDNESS: single
(D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:26:

```
Cys Asn Ile Ser Arg Ala Lys Trp Asn Asn Thr Leu Lys Gln Ile Asp
1               5                   10                  15
Ser Lys Leu Arg Glu Gln Phe
            20
```

(2) INFORMATION FOR SEQ ID NO:27:

(i) SEQUENCE CHARACTERISTICS:
(A) LENGTH: 23 amino acids
(B) TYPE: amino acid
(C) STRANDEDNESS: single
(D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:27:

```
Gln Ile Asp Ser Lys Leu Arg Glu Gln Phe Gly Asn Asn Lys Thr Ile
1               5                   10                  15
Ile Phe Lys Gln Ser Ser Gly
            20
```

(2) INFORMATION FOR SEQ ID NO:28:

(i) SEQUENCE CHARACTERISTICS:
(A) LENGTH: 24 amino acids
(B) TYPE: amino acid
(C) STRANDEDNESS: single
(D) TOPOLOGY: linear (ii) MOLECULE TYPE: peptide (i i i) HYPOTHETICAL: NO (i v) ANTI-SENSE: NO (v) FRAGMENT TYPE: internal (x i) SEQUENCE DESCRIPTION: SEQ ID NO:28:

Gly Asn Asn Lys Thr Ile Ile Phe Lys Gln Ser Ser Gly Gly Asp Pro
1               5                   10                  15

Glu Ile Val Thr His Ser Phe Asn
            20

(2) INFORMATION FOR SEQ ID NO:29:

(i) SEQUENCE CHARACTERISTICS:
    (A) LENGTH: 23 amino acids
    (B) TYPE: amino acid
    (C) STRANDEDNESS: single
    (D) TOPOLOGY: linear (i i) MOLECULE TYPE: peptide (i i i) HYPOTHETICAL: NO (i v) ANTI-SENSE: NO (v) FRAGMENT TYPE: internal (x i) SEQUENCE DESCRIPTION: SEQ ID NO:29:

Gly Asp Pro Glu Ile Val Thr His Ser Phe Asn Cys Gly Gly Glu Phe
1               5                   10                  15

Phe Tyr Cys Asn Ser Thr Gln
            20

(2) INFORMATION FOR SEQ ID NO:30:

(i) SEQUENCE CHARACTERISTICS:
    (A) LENGTH: 23 amino acids
    (B) TYPE: amino acid
    (C) STRANDEDNESS: single
    (D) TOPOLOGY: linear (i i) MOLECULE TYPE: peptide (i i i) HYPOTHETICAL: NO (i v) ANTI-SENSE: NO (v) FRAGMENT TYPE: internal (x i) SEQUENCE DESCRIPTION: SEQ ID NO:30:

Cys Gly Gly Glu Phe Phe Tyr Cys Asn Ser Thr Gln Leu Phe Asn Ser
1               5                   10                  15

Thr Trp Phe Asn Ser Thr Trp
            20

(2) INFORMATION FOR SEQ ID NO:31:

(i) SEQUENCE CHARACTERISTICS:
    (A) LENGTH: 20 amino acids
    (B) TYPE: amino acid
    (C) STRANDEDNESS: single
    (D) TOPOLOGY: linear (i i) MOLECULE TYPE: peptide (i i i) HYPOTHETICAL: NO (i v) ANTI-SENSE: NO (v) FRAGMENT TYPE: internal ( x i ) SEQUENCE DESCRIPTION: SEQ ID NO:31:

Leu Phe Asn Ser Thr Trp Phe Asn Ser Thr Trp Ser Thr Glu Gly Ser
1               5                   10                  15

Asn Asn Thr Glu
            20

( 2 ) INFORMATION FOR SEQ ID NO:32:

( i ) SEQUENCE CHARACTERISTICS:
        ( A ) LENGTH: 17 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:32:

Ser Thr Glu Gly Ser Asn Asn Thr Glu Gly Ser Asp Thr Ile Thr Leu
1               5                   10                  15

Pro ( 2 ) INFORMATION FOR SEQ ID NO:33:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:33:

Gly Ser Asp Thr Ile Thr Leu Pro Cys Arg Ile Lys Gln Phe Ile Asn
1               5                   10                  15

Met Trp Gln Glu
            20

( 2 ) INFORMATION FOR SEQ ID NO:34:

( i ) SEQUENCE CHARACTERISTICS:
        ( A ) LENGTH: 27 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:34:

Cys Arg Ile Lys Gln Phe Ile Asn Met Trp Gln Glu Val Gly Lys Ala
1               5                   10                  15

```
       Met  Tyr  Ala  Pro  Pro  Ile  Ser  Gly  Gln  Ile  Arg
                       20                      25
```

( 2 ) INFORMATION FOR SEQ ID NO:35:

( i ) SEQUENCE CHARACTERISTICS:
        ( A ) LENGTH: 24 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:35:

```
Val  Gly  Lys  Ala  Met  Tyr  Ala  Pro  Pro  Ile  Ser  Gly  Gln  Ile  Arg  Cys
 1              5                            10                       15
Ser  Ser  Asn  Ile  Thr  Gly  Leu  Leu
               20
```

( 2 ) INFORMATION FOR SEQ ID NO:36:

( i ) SEQUENCE CHARACTERISTICS:
        ( A ) LENGTH: 22 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:36:

```
Cys  Ser  Ser  Asn  Ile  Thr  Gly  Leu  Leu  Leu  Thr  Arg  Asp  Gly  Gly  Asn
 1              5                            10                       15
Asn  Asn  Asn  Glu  Ser  Glu
               20
```

( 2 ) INFORMATION FOR SEQ ID NO:37:

( i ) SEQUENCE CHARACTERISTICS:
        ( A ) LENGTH: 23 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:37:

```
Leu  Thr  Arg  Asp  Gly  Gly  Asn  Asn  Asn  Glu  Ser  Glu  Ile  Phe  Arg
 1              5                            10                       15
Pro  Gly  Gly  Gly  Asp  Met  Arg
               20
```

( 2 ) INFORMATION FOR SEQ ID NO:38:

( i ) SEQUENCE CHARACTERISTICS:
: ( A ) LENGTH: 22 amino acids
: ( B ) TYPE: amino acid
: ( C ) STRANDEDNESS: single
: ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:38:

```
Ile Phe Arg Pro Gly Gly Gly Asp Met Arg Asp Asn Trp Arg Ser Glu
1               5                   10                  15
Leu Tyr Lys Tyr Lys Val
            20
```

( 2 ) INFORMATION FOR SEQ ID NO:39:

: ( i ) SEQUENCE CHARACTERISTICS:
: : ( A ) LENGTH: 21 amino acids
: : ( B ) TYPE: amino acid
: : ( C ) STRANDEDNESS: single
: : ( D ) TOPOLOGY: linear : ( i i ) MOLECULE TYPE: peptide : ( i i i ) HYPOTHETICAL: NO : ( i v ) ANTI-SENSE: NO : ( v ) FRAGMENT TYPE: internal : ( x i ) SEQUENCE DESCRIPTION: SEQ ID NO:39:

```
Asp Asn Trp Arg Ser Glu Leu Tyr Lys Tyr Lys Val Val Lys Ile Glu
1               5                   10                  15
Pro Leu Gly Val Ala
            20
```

( 2 ) INFORMATION FOR SEQ ID NO:40:

: ( i ) SEQUENCE CHARACTERISTICS:
: : ( A ) LENGTH: 23 amino acids
: : ( B ) TYPE: amino acid
: : ( C ) STRANDEDNESS: single
: : ( D ) TOPOLOGY: linear : ( i i ) MOLECULE TYPE: peptide : ( i i i ) HYPOTHETICAL: NO : ( i v ) ANTI-SENSE: NO : ( v ) FRAGMENT TYPE: internal : ( x i ) SEQUENCE DESCRIPTION: SEQ ID NO:40:

```
Val Lys Ile Glu Pro Leu Gly Val Ala Pro Thr Lys Ala Lys Arg Arg
1               5                   10                  15
Val Val Gln Arg Glu Lys Arg
            20
```

( 2 ) INFORMATION FOR SEQ ID NO:41:

: ( i ) SEQUENCE CHARACTERISTICS:
: : ( A ) LENGTH: 12 amino acids
: : ( B ) TYPE: amino acid
: : ( C ) STRANDEDNESS: single -continued (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:41:

```
Ile Pro Ile His Tyr Cys Ala Pro Ala Gly Phe Ala
1               5                   10
```